United States Patent
Chen et al.

(10) Patent No.: US 10,921,168 B2
(45) Date of Patent: Feb. 16, 2021

(54) INTEGRATED MEASURING SYSTEM AND METHOD

(71) Applicant: WUHAN TAILIMEIXIN HEALTHCARE TECHNOLOGIES CO., LTD, Wuhan (CN)

(72) Inventors: Wenqiang Chen, Beijing (CN); Chao Cai, Wuhan (CN)

(73) Assignee: WUHAN TAILIMEIXIN HEALTHCARE TECHNOLOGIES CO., LTD., Wuhan (CN)

(*) Notice: Subject to any disclaimer, the term of this patent is extended or adjusted under 35 U.S.C. 154(b) by 413 days.

(21) Appl. No.: 15/757,398

(22) PCT Filed: Sep. 11, 2015

(86) PCT No.: PCT/CN2015/089440
§ 371 (c)(1),
(2) Date: Mar. 5, 2018

(87) PCT Pub. No.: WO2017/041294
PCT Pub. Date: Mar. 16, 2017

(65) Prior Publication Data
US 2018/0283913 A1 Oct. 4, 2018

(51) Int. Cl.
*G01C 19/00* (2013.01)
*G01D 18/00* (2006.01)
(Continued)

(52) U.S. Cl.
CPC .......... *G01D 18/008* (2013.01); *A61B 5/002* (2013.01); *A61B 5/0008* (2013.01); *A61B 5/01* (2013.01); *A61B 5/073* (2013.01); *A61B 5/6833* (2013.01); *A61B 90/98* (2016.02); *G01D 11/00* (2013.01); *G01D 18/00* (2013.01); *G01D 21/00* (2013.01);
(Continued)

(58) Field of Classification Search
None
See application file for complete search history.

(56) References Cited

U.S. PATENT DOCUMENTS

2009/0302940 A1 12/2009 Fuller et al.
2012/0291515 A1 11/2012 Stangelmayer et al.
(Continued)

FOREIGN PATENT DOCUMENTS

CN 1975343 A 6/2007
CN 101324453 A 12/2008
(Continued)

OTHER PUBLICATIONS

International Starch Report in PCT/CN2015/089440 dated Jun. 6, 2016, 6 pages.
(Continued)

*Primary Examiner* — Aditya S Bhat
(74) *Attorney, Agent, or Firm* — Metis IP LLC

(57) ABSTRACT

An integrated system and method for measuring and calibrating a parameter relating to an object or the environment is provided. The integrated measuring system may include a memory that may store a library of calibration formulas, a communication module that may retrieve information from a sensor, and a computing center that may perform calibration based on at least some of the received information.

19 Claims, 19 Drawing Sheets

(51) Int. Cl.
*A61B 5/01* (2006.01)
*A61B 5/07* (2006.01)
*G01D 21/00* (2006.01)
*A61B 5/00* (2006.01)
*A61B 90/98* (2016.01)
*G01D 11/00* (2006.01)

(52) U.S. Cl.
CPC ........... *A61B 5/0006* (2013.01); *A61B 5/0013* (2013.01); *A61B 2560/0214* (2013.01); *A61B 2560/0223* (2013.01); *A61B 2560/0238* (2013.01); *A61B 2560/0242* (2013.01)

(56) References Cited

U.S. PATENT DOCUMENTS

| | | | |
|---|---|---|---|
| 2014/0236366 A1 | 8/2014 | Livadaras et al. | |
| 2014/0275932 A1 | 9/2014 | Zadig | |
| 2014/0285416 A1* | 9/2014 | Priyantha | H04B 5/0037 345/156 |
| 2014/0308930 A1* | 10/2014 | Tran | H04W 4/18 455/414.1 |
| 2015/0005911 A1* | 1/2015 | Lake, II | G09B 19/0038 700/91 |
| 2015/0127738 A1* | 5/2015 | Thompson | H04W 4/80 709/204 |

FOREIGN PATENT DOCUMENTS

| | | |
|---|---|---|
| CN | 102458083 A | 5/2012 |
| CN | 103027671 A | 4/2013 |
| CN | 103115646 A | 5/2013 |
| CN | 103175566 A | 6/2013 |
| CN | 103177551 A | 6/2013 |
| CN | 104132685 A | 11/2014 |
| CN | 203983015 U | 12/2014 |
| CN | 104523245 A | 4/2015 |
| CN | 104655168 A | 5/2015 |
| CN | 105180995 A | 12/2015 |

OTHER PUBLICATIONS

Written Opinion in PCT/CN2015/089440 dated Jun. 6, 2016, 5 pages.
First Office Action in Chinese Application No. 201510581943.2 dated Jan. 26, 2017, 12 Pages.
The Forth Office Action in Chinese Application No. 201510581943.2 dated May 4, 2018, 9 Pages.
First Office Action in Chinese Application No. 201510578125.7 dated Feb. 22, 2017, 14 Pages.

* cited by examiner

| SOF | Request Flags | Command Code | Parameters | Data | CRC | EOF |

FIG. 9A

| SOF | Response Flags | Parameters | Data | CRC | EOF |

FIG. 9B data: n*(8 data bits + odd parity bit)

| S | b1 b2 b3 b4 b5 b6 b7 b8 | P | b1 b2 b3 b4 b5 b6 b7 b8 | P | b1 ...b8 | E |

LSB ← 1st data byte → 2nd data byte → nth byte

↑ Start of communication  ↑ End of communication

FIG. 9C

| Byte 0 | | | Byte 1 | | | | Byte n | | |
|---|---|---|---|---|---|---|---|---|---|
| Start | Bit 0 | Bit 1 | .. | Bit 6 | Bit 7 | P | Bit 0 | Bit 1 | .. | Bit 6 | Bit 7 | P | .. | Bit 0 | .. | Bit 7 | P | End |
| | Command or Data | | | Data | | | | Data | | |

| First part | | | Coefficients of the first segment | | | Difference values of the second segment | | | ... | Difference values of the last segment | | |
|---|---|---|---|---|---|---|---|---|---|---|---|---|
| Lower limit value α | Upper limit value β | Subsection-parameter γ | Initial coefficient A | Initial coefficient B | Initial coefficient C | Difference with the initial coefficients A | Difference with the initial coefficients B | Difference with the initial coefficients C | ... | Difference with the initial coefficients A | Difference with the initial coefficients B | Difference with the initial coefficients C |

FIG. 12A

| First part | | Second part |
|---|---|---|
| Lower limit value α | Upper limit value β | Order number of polynomial |

| Second part | | | |
|---|---|---|---|
| $a_0$ | $a_1$ | ... | $a_\gamma$ |

FIG. 12B

| First part | | | Second part | | | |
|---|---|---|---|---|---|---|
| Lower limit value α | Upper limit value β | Subsection-parameter γ | Resister value of first paragraph | Resister value of second paragraph | ... | Resister value of last paragraph |

FIG. 12C

| Reversed | AVG | TYPE | REF | C1 | C0 | 1701 |

INTEGRATED MEASURING SYSTEM AND METHOD

CROSS-REFERENCE TO RELATED APPLICATIONS

The present application is a U.S. National Stage entry under 35 U.S.C. § 371 of International Application No. PCT/CN2015/089440, filed on Sep. 11, 2015, designating the United States of America, the contents of which are hereby incorporated by reference.

TECHNICAL FIELD

The present disclosure relates to an integrated measuring system and method, more particularly, an integrated system and method for measuring and calibrating a parameter relating to an object or the environment.

BACKGROUND

There is an increasing need for monitoring the status of the environment or an object. Such an object may include, for example, a human being. To track or monitor some characteristics or parameters of the ambient environment or an object, one or more sensors may be installed or used. The sensors may either be analog or digital.

Information acquired by a sensor may need to be processed or calibrated using a device including, e.g., a microcontroller or a complicated circuit. The power to support the operation of such a sensor or device may be an issue to be considered, for example, when the sensor or device is portable and therefore need to be small and light. Thus it would be advantageous to develop a system and method for measuring one or more parameters relating to the environment or an object and calibrating the measured parameters. It would also be advantageous to have a measuring chip which is light-weighted and capable of harvesting energy from the ambient environment.

SUMMARY

The present disclosure relates to a system and process. Some embodiments of the present disclosure relate to a system or apparatus that may receive measurement data from one or more sensors. Exemplary data may include temperature, humidity, pressure, pulse, heartbeat, or the like, or any combination thereof. The system or apparatus may include a memory, a communication module, and a computing module. The memory may store a library of calibration formulas and calibration parameters. The communication module may be configured or used to retrieve information from a sensor. The computing center may be configured or used to select, based on the retrieved information, a calibration formula or a calibration parameter from the library and calibrate the retrieved information using the selected calibration formula or the calibration parameter.

In some embodiments, the system may include an energy harvesting module to harvest energy from the ambient environment. The energy harvested module may include a converter, an energy storage device, and a main power supply, and a power management unit. The converter may be configured or used to convert the energy harvested from the ambient environment into power in the form of, for example, direct current (DC). The energy storage device may be configured or used for storing the harvested energy or the power converted from the harvested energy. The main power supply may provide power for or drive at least some operations of the system. The power management unit may be configured or used to manage the flow of power within the system. For instance, the power management unit may monitor power connections and its battery charge, control the power flow to other parts of the system, manage the interface of the system, regulate an internal real-time clock (RTC), control sleep and power functions, or the like, or any combination thereof.

In some embodiments, the communication module may be configured or used for communicating with one or more external devices or external sensors. The communication module may include an RF interface, a sensor interface, an energy harvesting interface, a command signal interface, a clock input interface, or the like, or any combination thereof. The communication module may receive information from the ambient environment and store, process, and/or transmit that information to one or more of the external devices. The communication module may be operable to receive information from an external sensors or from an on-board sensor. The communication module may send control information to the external sensor or the on-board sensor.

In some embodiments, the memory may store information used in the system. The memory may include a user information storage unit, a processing data storage unit, a parameter storage unit, a program storage unit, and a log unit. The user information storage unit may be configured or used to store, for example, information of the measured object. The processing data storage unit may be configured or used to store, for example, the data that have already been processed or intermediate data held in the system. The parameter storage unit may be configured or used to store, for example, the coefficients for calibrating or some preconfigured parameters. The program storage unit may be configured or used to store, for example, execution codes, communication protocols, calibration formulas, or the like, or a combination there of. The log unit may be configured or used to store, for example, some other information including, for example, a trace log, a time stamp, or the like, or a combination thereof.

In some embodiments, the computing center may be configured or used for processing information received from, for example, an external sensor, an on-board sensor, or the like, or a combination thereof. The computing center may include a processing unit, a calibrating unit, and a computing unit. The processing unit may be configured or used to initialize the information to be processed. The calibrating unit may be configured or used to verify the information processed by the processing unit. The computing unit may be configured or used to map the value from the processing unit or the calibrating unit to be understood easily.

In some embodiments, an offline calibration mechanism is provided for calibrating the information received from, for example, an external sensor, an external device, an on-board sensor, or the like, or a combination thereof. A library including one or more calibration models may be provided. A calibration model may include a calibration formula. A calibration formula may include one or more calibration parameters that may relate to the received information. Merely by way of example, for first received information and second received information different from the first received information, a same calibration formula in combination with different calibration parameters may be used to perform the calibration. The calibration formulas may include the Steinhart-Hart equation, the Chebyshev fitting equation, a LUT (Look-Up-Table), an exponential equation, a Fourier equation, a Gaussian equation, an interpolant equation, a power equation, a rational equation, a smoothing spline equation, a sum of sine equation, the Weibul equation, or the like, or any combination thereof. The storing format of the calibration coefficients may change based on the calibration model. Furthermore, the calibration may be unnecessary.

In some embodiments, the system may include a patch. The patch may include a first layer and a second layer. The first layer may include a plastic film. The plastic film may be waterproof. The first layer may include an adhesive material for attaching the patch to an object to be measured. The first layer may be an upper layer. The patch may further include a third layer. The third layer may include an adhesive material for attaching the patch to the object to be measured. The second layer may include a chip that may be configured or used to calibrate information received from, for example, an external sensor, an external device, an on-board sensor, or the like, or a combination thereof.

These and additional features will be set forth in part by the description which follows, and manifest from the description, or may be learned by practice of the described disclosure.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIGS. 9A-9D show exemplary communication protocols according to some embodiments of the present disclosure;

FIG. 12A illustrates exemplary formats of the calibration parameters corresponding to the Steinhart-Hart equation according to some embodiments of the present disclosure;

FIG. 12B illustrates exemplary formats of the calibration parameters corresponding to Chebyshev fitting according to some embodiments of the present disclosure;

FIG. 12C illustrates exemplary formats of the calibration parameters corresponding to LUT according to some embodiments of the present disclosure;

DETAILED DESCRIPTION

Figure 1:
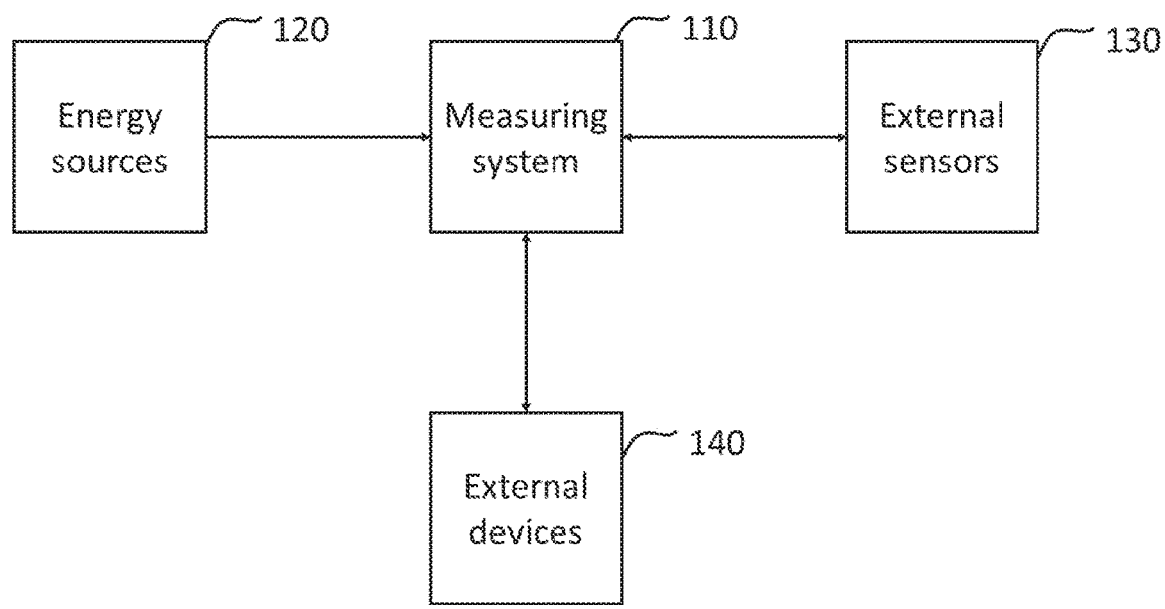
FIG. 1 shows a block diagram of a system according to some embodiments of the present disclosure.

After reading this description, it will become apparent to one skilled in the art how to implement the disclosure in various alternative embodiments and alternative applications. However, not all embodiments of the present disclosure are specifically described herein. It will be understood that the embodiments are presented by way of example only, and not limitation. As such, this detailed description of various alternative embodiments should not be construed to limit the scope or breadth of the present disclosure as set forth below.

It is to be understood that the aspects described below are not limited to specific systems, methods of making such systems or uses thereof as such may of course vary. It is also to be understood that the terminology used herein is for the purpose of describing particular aspects only and is not intended to be limiting.

According to the specifications and claims in the present application, unless otherwise specified in the content, articles such as "a," "an," and/or "the" do not necessarily indicate single forms, and also include plural forms. Generally, expressions such as "include" or "comprise" are only used to indicate numbered steps or elements. However, listing of these steps and elements is not exclusive, and methods or devices may include other steps or elements.

The present disclosure may be applied in many areas, e.g., remote sensing, non-destructive evaluation, surveillance, physiological features monitoring, environment monitoring, smart home, wearable devices, or the like, or any combination thereof. Merely by way of example, the present disclosure may relate to a system, apparatus, and method for measuring environment related or human related parameters including, for example, temperature, noise factor, Particulate Matter 2.5 (PM2.5), density of harmful substance, blood pressure, etc. The following description is provided in the exemplary context of temperature measurement. However, it is understood that it is for illustration purposes, and is not intended to limit the scope of the present disclosure. For instance, the system, apparatus, or method disclosed herein may be used in a food manufacturing factory for monitoring the quality of the food by measuring, for example, the temperature of the food produced, or the temperature of the work place where the food is produced in real time. It may also be used in transportation for monitoring, for example, the status of goods using a monitoring apparatus provided in this disclosure. It is understood that the description/example above is for illustration purposes, and is not intended to limit the scope of the present disclosure. The method for parameter measuring may involve a calibration technique. The sensed parameters may be calibrated to improve the accuracy of the result. In some embodiments, the calibration may be performed offline. The calibration may be performed using various calibrating methods in accordance with the need of a user. The system, apparatus and method may involve an energy harvesting component and method. The following description is provided with reference to calibrating in connection with the system, apparatus, and method for illustration purposes, and is not intended to limit the scope of the present disclosure.

FIG. 1 shows a block diagram of a system according to some embodiments of the present disclosure. A system 110 may interact with one or more devices and the ambient environment. For instance, the system 110 may be connected, coupled, or communicate with one or more energy sources 120, and/or one or more external sensors 130, and/or one or more external devices 140. The descriptions with reference to the system 110 below may be applicable to the embodiments relating to an apparatus.

The system 110 may be configured or used to harvest energy from one or more energy sources 120 and transform the harvested energy from one form to another. Merely by way of example, the system 110 may harvest energy in the form of radio frequency (RF) energy and transformed the harvested RF energy into an electric power (for example, direct current (DC)). Exemplary energy sources 120 may include thermal energy, solar energy, vibration energy, radio frequency (RF) energy, bioenergy, or the like, or any combination thereof.

The system 110 may be connected with or attached to one or more external sensors 130. The connection or attachment may be achieved via, for example, one or more of adhesive, clip(s), binding(s), tape, or the like, or any combination thereof. The external sensors 130 may also be electrically and/or thermally connected with or coupled to the external devices 140 using for example, a hard-wire, a wireless connection, a thermocouple, or the like, or any combination thereof. In some embodiments, the system 110 may include an on-board sensor. The system 110 may be configured or used to convert the information from the external sensor 130 or an on-board sensor to various formats including, for example, analog, frequency, a ramp rate, a duty cycle, a serial output, a logic output, or the like, or any combination thereof. A serial output may be communicated via, for example, an inter-integrated circuit (I2C or IIC) interface, a serial peripheral interface (SPI), a Timer External Source Pin, an EXIT Pin, a General Purpose Input/output (GPIO), a Single Wire, a Universal Synchronous Asynchronous Receiver Transmitter (USART), a Universal Asynchronous Receiver/Transmitter (UART), etc. In some embodiments, the system 110 may convert information measured by a sensor to frequency using an oscillatory circuit. Exemplary oscillatory circuits may include a Schmidt trigger oscillator, a Triode oscillation circuit, a Ring oscillator, an oscillatory circuit with compensating circuit, a conventional oscillatory circuit, a Wien bridge oscillator, an oscillator including a 555 timer, a positive feedback oscillation circuit, or the like, or any combination thereof. In some embodiments, the system 110 may be configured or used to receive and process information measured by an external sensor 130 or an on-board sensor. The processed information may be stored and/or sent to an external device 140. In some embodiments, the system 110 may send control signals to an external sensor 130 or an on-board sensor. Exemplary external sensors 130 may include a temperature sensor, a humidity sensor, a velocity sensor, an accelerometer (acceleration sensor), a proximity sensor, a thermal sensor, a gas sensor, a pressure sensor, a motion sensor, a biological information sensor, an electromagnetic sensor, a strain sensor, a resistance sensor, an electromechanical sensor, a magneto-resistive sensor, a Hall Effect sensor, a current measurement sensor, or the like, or any combination thereof. An on-board sensors may include any one of those illustrated above.

The system 110 may communicate with one or more external devices 140. In some embodiments, the system 110 may receive a control signal from an external device 140 and send information to the external device 140. The system 110 may process the information received from an external sensor 130 based on the control signal, or transfer information to, for example, a mobile phone, a pad, a Personal Digital Assistant (PDA), in response to the control signal. The system 110 may be configured to be connected or communicate with multiple external devices 140 simultaneously. Exemplary external devices 140 may include a mobile phones, a personal computer (PC), a smart watch, a tablet, a smart band, or the like, or any combination thereof.

It should be noted that the description of the system 110 and its behavior or interaction with the ambient environment and/or devices is provided for illustration purposes. For persons having ordinary skills in the art, adjustments and modifications may be made without departing from the principle or spirit of the present disclosure. Therefore, it is given that the present disclosure should not be limited by the specific description herein. For example, an external sensor 130 may be integrated in the system 110. Such alternatives, modifications, and variations will also be in the scope of this disclosure.

Figure 2:
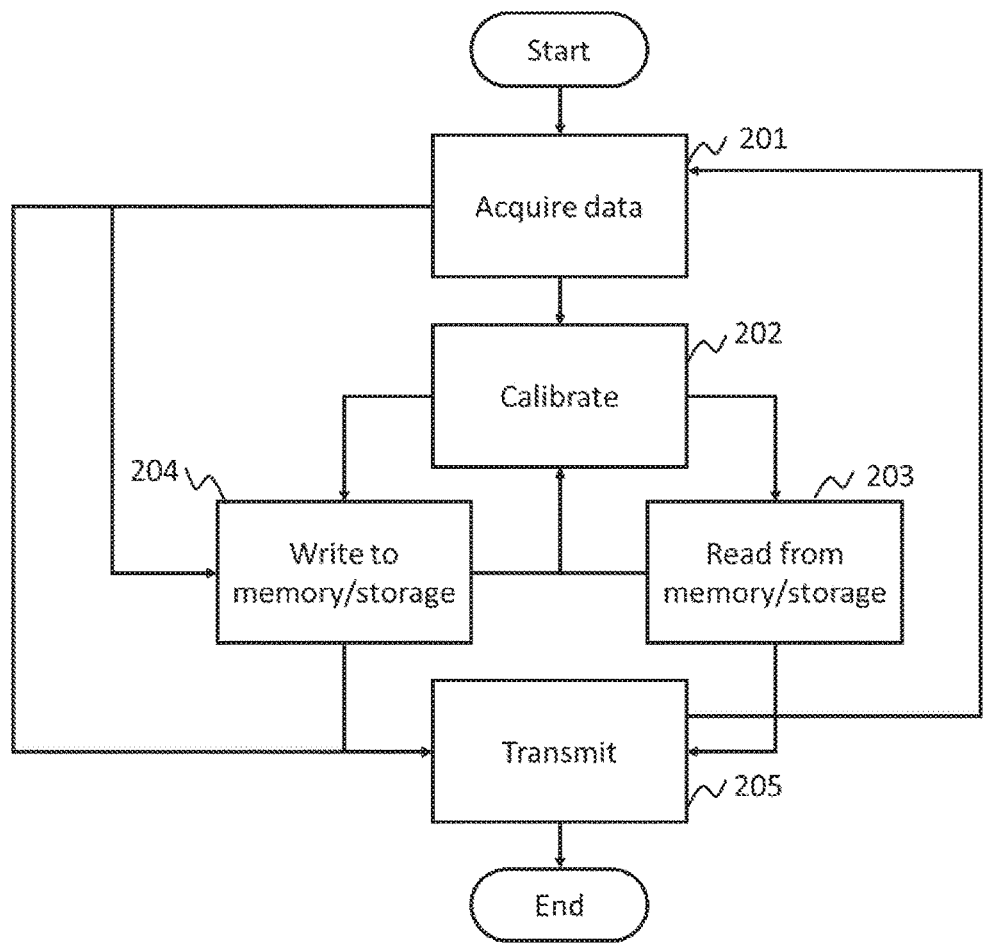
FIG. 2 is a flowchart illustrating a process for data reading and writing of the system according to some embodiments of the present disclosure.

FIG. 2 is a flowchart illustrating a process for data reading and writing in connection with the system 110 according to some embodiments of the present disclosure. The system 110 may acquire data regarding an object or the ambient environment in step 201. Exemplary data may include temperature, humidity, velocity, gas composition, pressure, biological information, acceleration, motion, or the like, or any combination thereof. In some embodiments of the present disclosure, the system 110 may be connected with an external sensor 130 to receive data through a sensor interface. The interface may include an analog-to-digital converter (ADC), SPI, IIC, USART, UART, a Timer External Source Pin, an EXIT Pin, a General Purpose Input/output (GPIO), a Single Wire, or the like, or any combination thereof. Alternatively, the system 110 may have one or more built-in sensors (also referred to as on-board sensors). The system 110 may measure a parameter of interest using such a built-in sensor. The acquired data may include the measured parameter.

In step 202, the system 110 may perform a calibration of the acquired data. Calibration may be performed on the basis of one or more parameters and one or more calibration modes. In some embodiments of the present disclosure, a high precision calibration may be performed. Calibration may be performed in accordance with one or more calibration formulas. Exemplary calibration formulas may include the Steinhart-Hart equation, the Chebyshev fitting equation, a LUT (Look-Up-Table), an exponential equation, a Fourier equation, a Gaussian equation, an interpolant equation, a power equation, a rational equation, a smoothing spline equation, a sum of sine equation, the Weibul equation, or the like, or any combination thereof. The calibrated data may be written into a memory in step 204. Data, for example, the calibration parameters, the predetermined information, or control information, may be read or retrieved in step 203 from a memory via, for example, a communication module. The calibration step may be repeated by returning to step 202. The data may be acquired from a built-in sensor or an external sensor 130. In some embodiments, the data may be read from a memory, e.g., a memory of the system 110.

In step 205, the calibrated data may be transmitted. The calibrated data may be transmitted via a wired connection or wirelessly. In some embodiments, the calibrated data may be transmitted to a receiving device through a cable network. In some embodiments, the calibrated data may be transmitted wirelessly, such as a WiFi, communication network, an acoustic communication, a visual light communication, a vibration communication, or the like, or any combination thereof. Alternatively, the calibrated data may be transmitted by employing a near-field communication technique including, for example, near-field communication (NFC), radio frequency identification (RFID), or the like, or any combination thereof. From step 205, the system 110 may return to step 201 for a next round of data processing. In some embodiments, the data acquisition, data reading, and/or writing may be terminated by one or more control signals.

It should be noted that the flowchart described herein is provided for illustration purposes, and not intended to limit the scope of the present disclosure. For persons having ordinary skills in the art, various variations and modifications may be performed with a reasonable understanding of the present disclosure. However, those variations and modifications may not depart the spirit and scope of the present disclosure. For example, apart from concurrent execution of step 203 and step 204, step 203 and step 204 may be performed sequentially regardless of the order. Furthermore, from step 201, steps 202-204 may be skipped and the sensed data may be transmitted directly in step 205 without calibration. As another example, step 204 may be skipped, and the calibrated data may be transmitted to a user or an external device 140 and not stored in a memory of the system 110. Still as another example, the acquired data in step 201 may be written to memory/storage directly without being calibrated in step 202.

Figure 3:
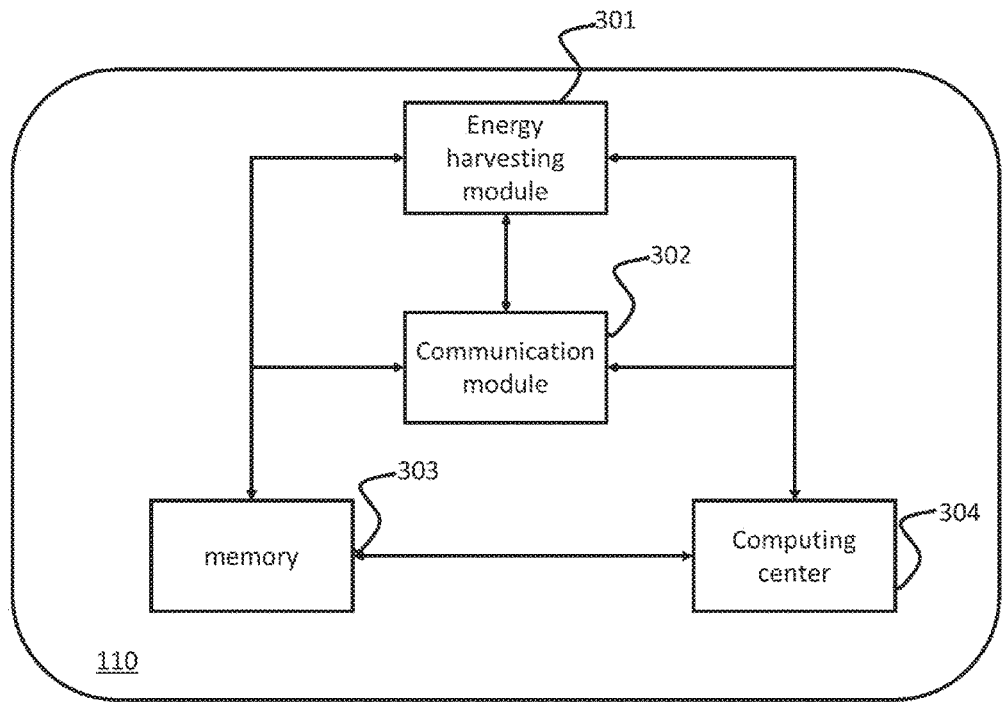
FIG. 3 illustrates an exemplary system according to some embodiments of the present disclosure.

FIG. 3 illustrates an exemplary diagram of the system 110 according to some embodiments of the present disclosure. The system 110 may be configured or used to harvest energy. The harvested energy may provide power for at least some of the operations of the system 110 itself. For instance, the harvested energy may provide power for the system 110 to acquire information or data from an external sensor 130, to process the information or data, to communicate with an external device 140, or the like, or any combination thereof. The information or data may include one or more parameters relating to an object or the environment. As illustrated, the system 110 may include an energy harvesting module 301, a communication module 302, a memory 303, and a computing center 304.

The energy harvesting module 301 may be configured or used to energy harvest and management. Such energy may be used for powering or driving at least some operations of the system 110. Exemplary operations may include the operations of the communication module 302, the memory 303, the computing center 304, or any other circuit in the system 110. The energy harvesting module 301 may be operable to receive information from, e.g. one or more other modules of the system 110 or an external device 140, and allocate the harvested energy based on such information. It should be noted that the energy harvesting module 301 may either harvest energy independently or in coordination with the energy harvesting interface in the communication module 302.

The communication module 302 may include an RF interface, a sensor interface, an energy harvesting interface, a command signal interface, a clock input interface, or the like, or any combination thereof. In some embodiments, the RF interface may configured to communicate with an external device or harvest energy from the ambient environment. The sensor interface may be configured to communicate with external sensor or on-board sensor. The communication module 302 may harvest energy from the environment. The communication module 302 may be configured or used to receive information from one or more external devices 140 or one or more external sensors 130. Information from the external devices 140 may include control information, command information, initial information, configuration information, termination information, or the like, or any combination thereof. The communication module 302 may also be configured or used to receive information from one or more components of the system 110 including, for example, the memory 303, the computing center 304, or the like, or any combination thereof. The communication module 302 may send information, e.g., information received from components of the system 110, to the external devices 140 or the external sensors 130. The communication module 302 may output information to the external devices 140, or output control information to the external sensors 130. Furthermore, the communication module 302 may be configured to transfer information among external sensor, external device and the system.

In some embodiments, the communication module 302 may include a switching unit (not shown in the figure) for parsing the information from the external device 140 and/or an external sensor 130, and framing the parsed information to a readable format for the external device 140. For example, the switching unit may parse information from an external device 140 and an external sensor 130 so that readable information for the memory 303 and the computing center 304 may be generated. As another example, the switching unit may be configured or used to encode information to a desired format for the external device 140 and/or the external sensor 130. The information may be framed according to an RFID protocol when an external device 140 is an RFID reader. The switching unit may be configured to frame information to various frame formats simultaneously when there are various external devices 140 which may be based on different protocols. Some exemplary protocol frame formats are illustrated in FIGS. 9A-9D and the description thereof.

In some embodiments, the computing center 304 may be connected or communicate with an external sensor 130 or an external device 140 via the communication module 302.

Furthermore, the computing center 304 may configure some settings for an external sensor 130 including, for example, the sampling rate, range or accuracy.

The memory 303 may be configured or used for storing information for the system 110. The information may include calibration parameters, stored format information, a communication protocol, command information, configuration information, program information, information received from an external sensor 130, information received from an external device 140, information received from the computing center 304, or the like, or any combination thereof. The memory of the system 110 may include a dynamic storage device configured to store information and instructions to be executed by the processor of a system-on-chip (SoC, for example, a chipset including a processor), other processors (or computing units), or the like, or any combination thereof. The memory may also be used to store temporary variables or other intermediate information during execution of instructions by the processor(s). Part of or the entire memory may be implemented as a Dual In-line Memory Modules (DIMMs), a flash, a cache, a buffer, a ROM, a RAM, a register, a magnetic disk, an optical disc, a hard disk, a floppy disk, an electron storage, a film memory, a phase change memory, a cloud disk, a NAND flash memory, a NOR flash memory, and the RAM may be one or more of the following types of memory: static random access memory (SRAM), Burst SRAM or SynchBurst SRAM (BSRAM), dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDECSRAM, PCIOO SDRAM, Double Data Rate SDRAM (DDR SDRAM), Enhanced SDRAM (ESDRAM), SyncLink DRAM (SLDRAM), Direct Rambus DRAM (DRDRAM), Ferroelectric RAM (FRAM), or any other type of memory device. The memory may also include read-only memory (ROM) and/or another static storage device configured to store static information and instructions for the processor of the SoC and/or other processors (or computing units). Further, the memory or electronic storage media may include a magnetic disk, optical disc or flash memory devices to store information and instructions.

In some embodiments, the SoC may be part of a core processing or computing unit of a component of or accessible from the system 110. The SoC may be configured or used to receive and process input data and instructions, provide output and/or control other components of the system. In some embodiments, the SoC may include a microprocessor, a memory controller, a memory, and a peripheral component. The microprocessor may further include a cache memory (for example, SRAM), which along with the memory of the SoC may be part of a memory hierarchy to store instructions and data. The microprocessor may also include one or more logic modules such as a field programmable gate array (FPGA) or other logic array. Communication between the microprocessor in the SoC and memory may be facilitated by the memory controller (or chipset), which may also facilitate in communicating with the peripheral component, such as a counter-timer, a real-time timer, a power-on reset generator, or the like, or a combination thereof. The SoC may also include other components including, but not limited to, a timing source (e.g., an oscillator, a phase-locked loop, or the like), a voltage regulator, a power management circuit, a comparator, a frequency multiplier, a Phase Locked Loop (PLL), an Analog to Digital Converter (ADC), a Digital to Analog Converter (DAC), a Float Point Unit (FPU), a serial port, Infrared Data Association (IrDA), Directional Memory Access (DMA), or the like, or a combination thereof.

Merely by way of example, the system 110 may include a wearable or portable device in the form of, for example, a patch. See, for example, the patch 1401 illustrated in FIG. 14. The wearable or portable device may include a SoC. The wearable or portable device may include or communicate with one or more sensors (for example, external sensors 130 or on-board sensors) or one or more external devices 140. Exemplary sensors may include a photoelectric sensor, a conductance sensor, or the like, or a combination thereof. The SoC may process information acquired through one or more of the sensors. The acquired information may be one or more biological signals, environmental signals, or the like, or any combination thereof. The SoC may calibrate the acquired signals.

The computing center 304 may be configured or used to process the information received via, e.g., the communication module 302. The computing center 304 may perform various operations including, for example, sampling analog signals, initializing the sampled information, computing initial parameters, calibrating initial parameters, or the like, or any combination thereof. The computing center 304 may exchange information with components of the system 110 (e.g., the memory 303), an external device 140, an external sensor 130, or the like, or any combination thereof. The information exchange may be achieved via the communication module 302.

The features described in the disclosure are not all-inclusive and, in particular, many additional features will be apparent to one of ordinary skill in the art in view of the drawings and specification. For example, the system 110 may also include one or more on-board (or built-in) sensors. In some embodiments, such an on-board sensor may be powered by energy harvested by the energy harvesting module 301. An on-board sensor may be configured or used to monitor or measure one or more parameters relating to an object or the environment. The parameters may be processed by the communication module 302 or the computing center 304.

Figure 4:
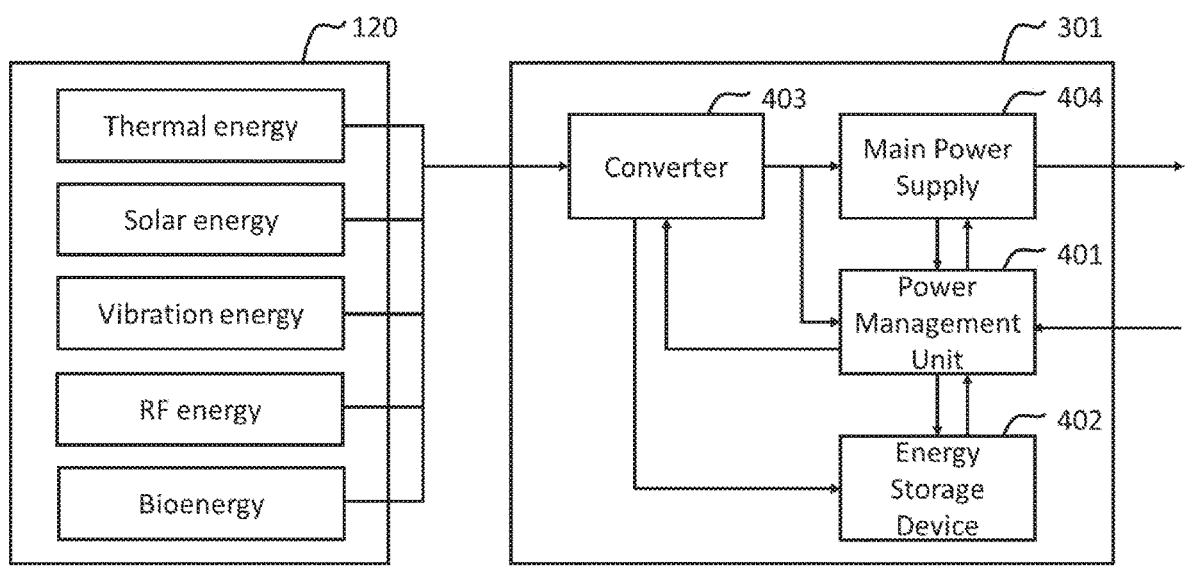
FIG. 4 is a block diagram of an energy harvesting module and an exemplary interaction with energy sources according to some embodiments of the present disclosure.

FIG. 4 is a block diagram of the energy harvesting module 301 and its interaction with energy sources 120 according to some embodiments of the present disclosure. The energy harvesting module 301 may include a unit for harvesting a form of energy (for example, a solar panel/cell), a capsule, a circuit, or the like, or any combination thereof. The energy harvesting module 301 may be configured or used to supply power to the system by harvesting energy from the ambient environment. Exemplary energy sources 120 from the ambient environment are illustrated in FIG. 4. Exemplary energy sources 120 may include thermal energy, solar energy, vibration energy, RF energy, bioenergy, or the like, or any combination thereof. In some embodiments, the energy harvesting module 301 may harvest thermal energy and convert it to power by exploiting the thermoelectric effect generating a current or a voltage. For example, a human body may constitute a heat source for power generation according to the thermoelectric effect. In some embodiments, the energy harvesting module 301 may harvest solar energy and convert it to power by exploiting the photovoltaic effect. A solar panel or a photo sensor (or sensor array) may be utilized to harvest solar energy and generate power. For vibration energy, power such as an electrical voltage or current may be generated from vibration or mechanical strains using a piezoelectric material. Merely by way of example, vibration energy when there is a continuous mechanical motion or human motion may be harvested and converted to power. Bioenergy from the degradation of an organic material may be used to generate power. For example, the system 110 may include an organic cover that may release power to power or drive at least some operations of the system when the cover degrades. The energy harvest or power generation may be either continuous or sporadic.

In some embodiments, radio frequency (RF) signals in the ambient environment may be harvested and converted to power. Exemplary RF signals may include a wireless communication signal (a signal generated from a network provided by a communication service provider such as a cellular network), a broadcasting signal, a WiFi signal generated from a WiFi network, a Bluetooth signal, a ZigBee signal, an infrared signal, or the like, or any combination thereof. The frequency of a signal usable according to the present disclosure may range from 3 kHz to 10 kHz, or from 30 kHz to 300 kHz, or from 300 kHz to 3000 kHz, or from 3 MHz to 30 MHz, or from 30 MHz to 300 MHz, or from 300 MHz to 3000 MHz, or from 3 GHz to 30 GHz, or from 30 GHz to 300 GHz, or from 300 GHz to 3000 GHz, or from 13.56 MHz to 900 MHz, or from 1 GHz to 1.2 GHz, or from 1.5 GHz to 2 GHz. The RF signals may be received using an antenna. The antenna may include a high-gain antenna, an isotropic antenna, a multiband antenna, a monopole antenna, a dipole antenna, an array antenna, a loop antenna, an aperture antenna, a travelling wave antenna, a log-periodic antenna, a flexible antenna, a horn antenna, a folded dipole antenna, a covered slot antenna, a circular patch antenna, a meander antenna, a planar inverted F-antenna, or the like, or any combination thereof. The antenna may include a flexible material solar cell (for example, a photovoltaic antenna), or a flexible antenna, etc.

The energy harvesting module 301 may be configured or used to receive energy from an energy source 120 and convert the energy into power in the form of, for example, an electrical voltage or current. The power may be stored in an energy storing device or drive at least some operations of the system 110. The energy harvesting module 301 may include a converter 403, a main power supply 404, a power management unit 401, and an energy storage device 402. The energy harvesting module may be configured in forms including, for example, a solar panel, a thermoelectric device, a piezoelectric device, a cover made of an organic material, or the like, or any combination thereof.

The converter 403 may receive energy from an energy source 120 and convert the energy into power in the form of, for example, an electric power (voltage or current). In some embodiments, the converter 403 may be connected to an antenna that may receive RF signals from the ambient environment, and a circuit that may convert the RF signals into direct current (DC). The antenna may include a high-gain antenna, an isotropic antenna, a multiband antenna, a monopole antenna, a dipole antenna, an array antenna, a loop antenna, an aperture antenna, a travelling wave antenna, a log-periodic antenna, a flexible antenna, a horn antenna, a folded dipole antenna, a covered slot antenna, a circular patch antenna, a meander antenna, a planar inverted F-antenna, or the like, or any combination thereof. The circuit of the converter 403 may be a diode or transistor based circuit, such as, for example, a rectifier circuit with charge pumps. It is to be noted that the above mentioned examples of the converter 403 are provided for illustration purposes, and not intended to limit the scope of the present disclosure.

The converter 403 may be configured to covert harvested energy to a current signal or a voltage signal. Merely by way of example, the converter 403 may produce a current signal and the current signal may be supplied to the main power supply 404, the power management unit 401, and/or the energy storage device 402. The energy storage device 402 may receive the current signal from the converter 403 and storage the current signal. The energy storage device 402 may be configured as a battery or an energy storage circuit employing one or more capacitors, for example, one or more super capacitors. The power management unit 401 may be configured or used to set or maintain a power usage schedule for the system 110. The power management unit 401 may receive the current signal from the converter 403. The power management unit 401 may turn the converter 403 on or off by sending one or more control signals thereto. The power management unit 401 may be bi-directionally connected with the energy storage device 402. The power management unit 401 may receive a power signal, for example, a current signal, from the energy storage device 402. The power management unit 401 may also send a control signal to the energy storage device 402. The power management unit 401 may be bi-directionally connected with the main power supply 404. The power management unit 401 may process the received power signal and convey the processed power signal to the main power supply 404. For example, the power management unit 401 may be configured to monitor power connections and its battery charge, control power to other parts of the system, manage the interface of the system, regulate an internal real-time clock (RTC), control sleep and power functions, the like, or any combination thereof. The main power supply 404 may send a power signal to the power management unit 401. The main power supply 404 may be configured or used to supply power to the system 110. In some embodiments of the present disclosure, the main power supply 404 may supply power to the system 110 by receiving a power signal from the converter 403 without storing the power relating to the power signal into the energy storage device 402. In some embodiments, the main power supply 404 may supply the system 110 with a power signal received from the energy storage device 402 via the power management unit 401. In some embodiments, a power schedule algorithm according to a feedback signal from the system 110 may be used to determine whether the converter 403 send a power signal to the main power supply directly 404 or store the power relating to the power signal into the energy storage device 402.

For example, when the system 110 is performing a task that needs or consumes a large amount of power, a feedback signal may request the power management unit 401 to utilize the energy stored in the energy storage device 402. Conversely, when a task performed by the system 110 needs or consumes a small amount of power, the converter 403 may supply power to the system 110 by sending a power signal directly to the main power supply 404, not storing the generated power relating to the power signal in the energy storage device 402.

The features described in the disclosure are not all inclusive and, in particular, many additional features will be apparent to one of ordinary skill in the art in view of the disclosure.

Figure 5:
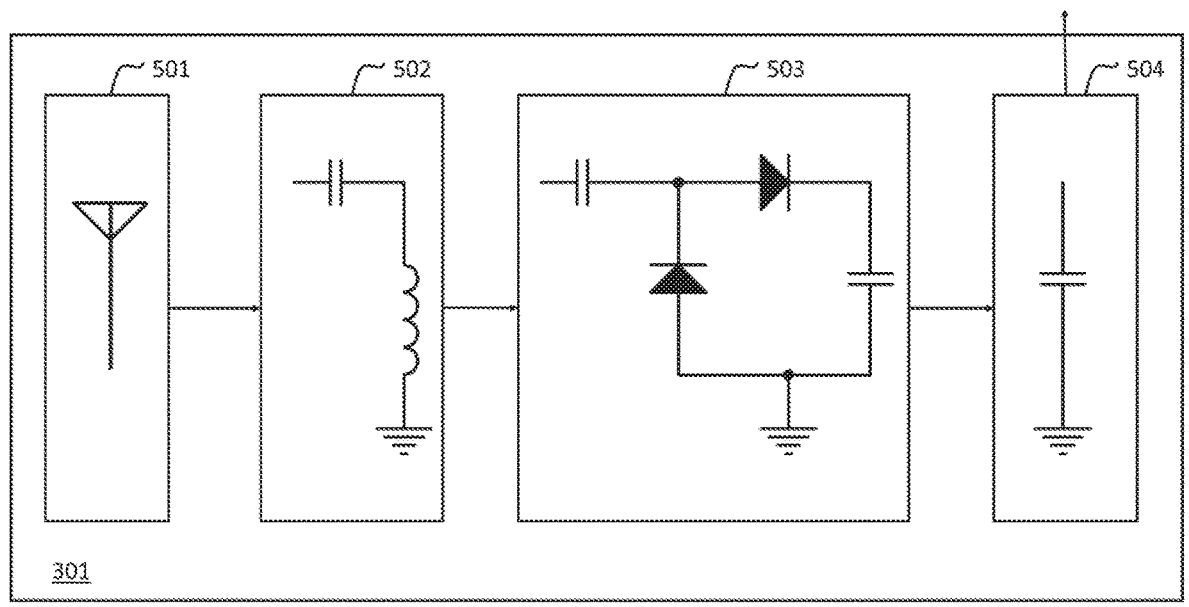
FIG. 5 depicts a schematic diagram of an energy harvesting module according to some embodiments of the present disclosure.

FIG. 5 depicts a schematic diagram of an exemplary energy harvesting module 301 according to some embodiments of the present disclosure. The energy harvesting module 301 may include an antenna 501, a matching circuit 502, a charge pump 503, and a charge tank 504. The antenna 501 may be configured or used to receive ambient RF signals of a suitable frequency or of a frequency range. For example, the antenna 501 may receive high frequency oscillation signals, RF signals running at 53 MHz, or within a range of 3 MHz to 30 MHz, or the like, or any combination thereof. The antenna may include a high-gain antenna, an isotropic antenna, a multiband antenna, a monopole antenna, a dipole antenna, an array antenna, a loop antenna, an aperture antenna, a travelling wave antenna, a log-periodic antenna, a flexible antenna, a horn antenna, a folded dipole antenna, a covered slot antenna, a circular patch antenna, a meander antenna, a planar inverted F-antenna, or the like, or any combination thereof.

Figure 6:
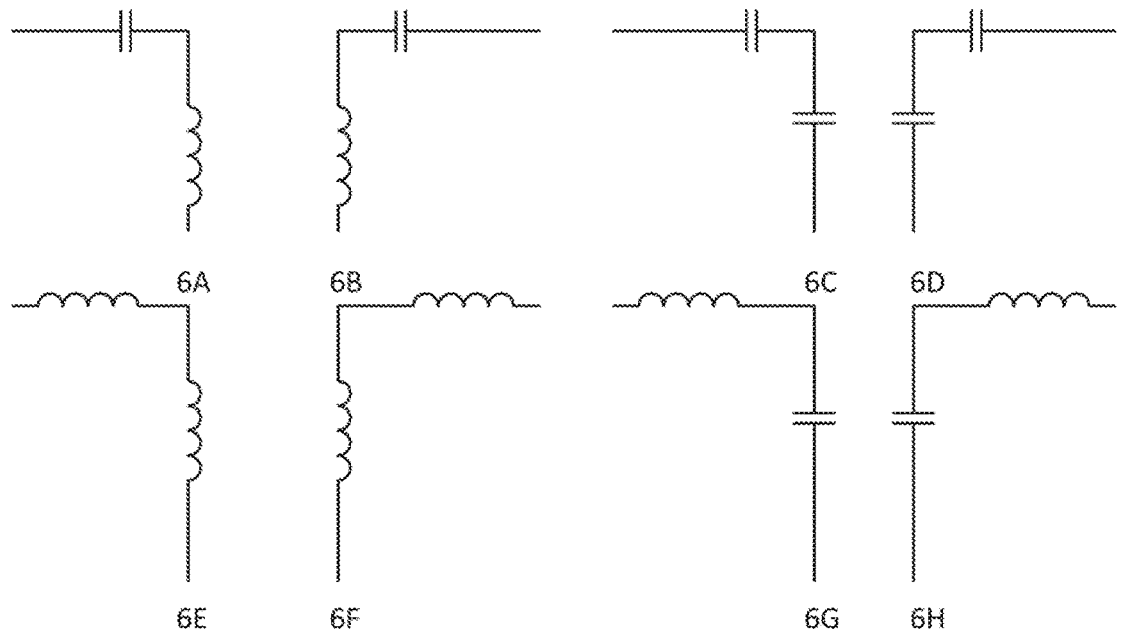
FIG. 6 shows exemplary matching circuit according to some embodiments of the present disclosure.

The matching circuit 502 may be coupled to the antenna 501 and configured or used to assist the antenna 501 in receiving RF signals. Moreover, the matching circuit 502 may be used for filtering clutters by interference, which may obscure undesired signals. As illustrated in the figure, the matching circuit 502 may be implemented as a two-component matching circuit including a capacitor and an inductor. It should be noted that the matching circuit 502 illustrated in the figure is for the purposes of illustration, not intended to limit the scope of the present disclosure. Although a two-component matching circuit 502 is illustrated in FIG. 5, variations and modifications may be made by persons having ordinary skill in the art without departing from the scope of the present disclosure. Exemplary variations and modifications are shown in FIG. 6. The matching circuit 502 may be implemented as illustrated in 6A, 6B, 6C, 6D, 6E, 6F, 6G, 6H, or the like, or any combination thereof. Apart from the implementation of a two-component circuit, the matching circuit 502 may alternatively be implemented as a L-matching circuit, a T-matching circuit, a PI-matching circuit, or the like, or any combination thereof (not shown in the figure). In some embodiments, the matching circuit 502 may be used as an impedance matching circuit and provide an enhanced and/or predetermined impedance match between the output of the antenna 501 and the input of a downstream circuit. For example, the matching circuit 502 may be high-Q to passively increase the voltage amplitude and Signal to Noise Rate (SNR) for communication. Additionally, the matching circuit 502 may also be low-Q to broaden the bandwidth of harvestable RF signals for improving the energy harvesting efficiency. In some embodiments, the matching circuit 502 may be configured such that the impedance may be of at least 95% of the ideal impedance value to achieve a high passive voltage gain from high-Q matching and a higher power from low-Q matching.

In some embodiments, there may be an absolute value circuit (not shown in the figure) for outputting a positive flow signal. The absolute value circuit may be implemented via an operational amplifier circuit, a diode, etc. The output of the absolute value circuit may be a positive voltage that represents the absolute value of the input, whether the input is positive or negative.

The charge pump 503 may be configured or used to amplify received RF signals. As illustrated in the figure, the charge pump 503 may include two diodes and two capacitors. After a received RF signal is converted to a power signal, the charge pump 503 may amplify the power signal and output, for example, a voltage of a desired magnitude, for example, 1.8 V-3.3 V. In some embodiments, the charge pump 503 may be configured or used to double the effective amplitude of the AC voltage. Furthermore, the charge pump 503 may be configured as a multi-stage charge pump. For instance, the charge pump 503 may include several stages of the circuit shown in the figure, for example, five stages or six stages. Alternatively, the charge pump 503 may also be configured or used to convert the energy to a DC voltage and accumulate the energy in the charge tank 504. The charge pump 503 may include a rectifier circuit (not shown in the figure). The rectifier circuit (also referred to as rectifier) may include a center-feed transformer, a rectifying diode bridge, a single-phase rectifier, a three-phase rectifier, a voltage-multiple rectifier, or the like, or any combination thereof. The rectifier may be configured or used to stabilize the output.

The charge tank 504 may be coupled to the charge pump 503 and store collected direct current signals or voltage signals from the charge pump 503. The charge tank 504 may be implemented by employing, for example, a capacitor, a battery, a bank, or the like, or any combination thereof. The charge tank 504 may supply power to the system 110 by outputting current signals or voltage signals.

The above description of the circuit of the energy harvesting module is provided for illustration purposes, and not intended to limit the scope of the disclosure. For example, the charge pump 503 and the rectifier circuit may be integrated into one circuit. As another example, there may be no charge tank 504. The collected power signal may be transferred to power that may drive at least some operations of the system 110 directly. However, such variations and modifications do not depart from the scope and spirit of the present disclosure.

Figure 7:
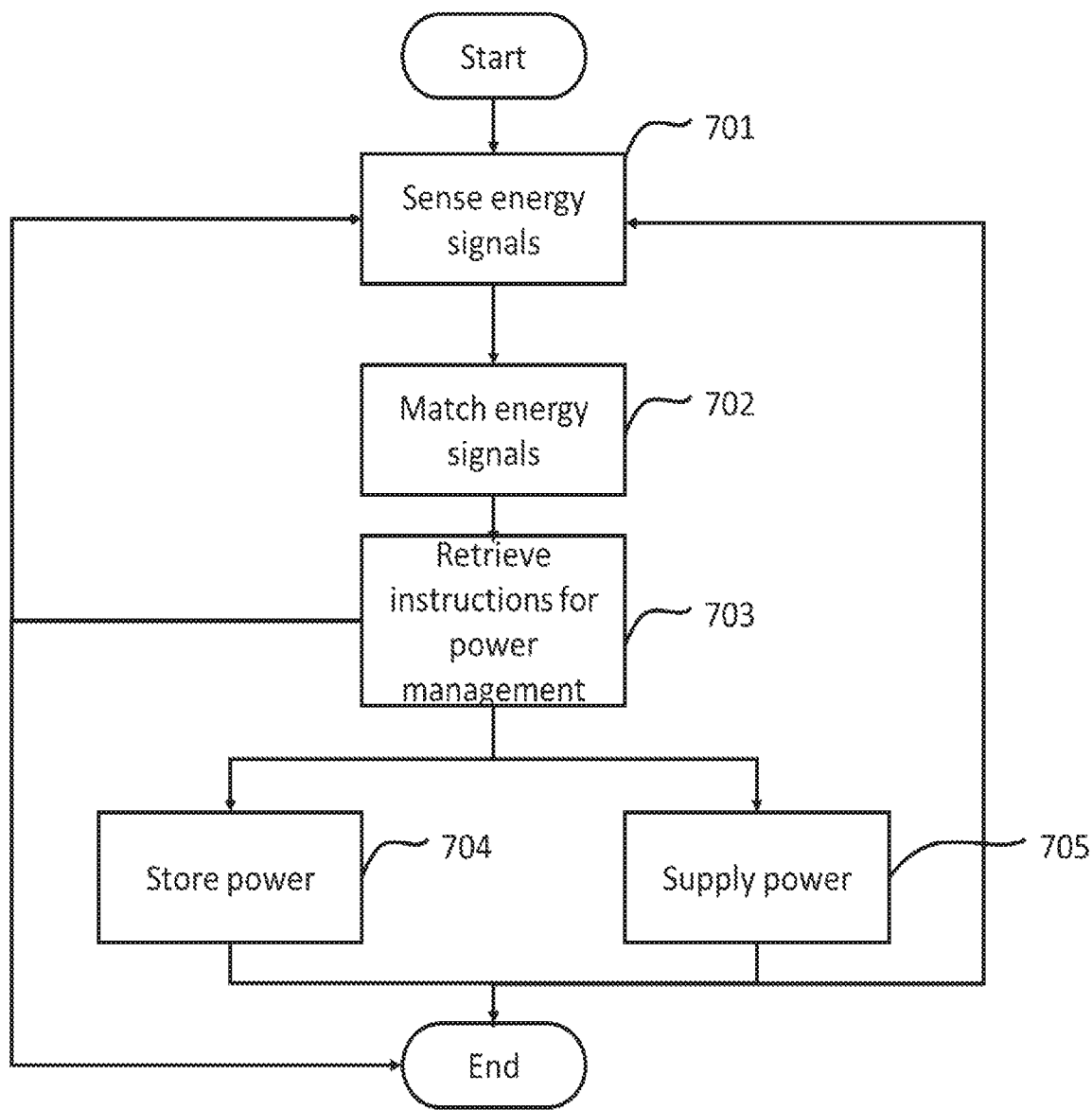
FIG. 7 shows a flowchart of a process for energy harvesting according to some embodiments of the present disclosure.

FIG. 7 shows a flowchart describing a process for energy harvesting according to some embodiments of the present disclosure. As shown in the figure, the process may start with sensing energy signals in the ambient environment. Exemplary energy signals may include solar signals, thermal signals, vibration signals, radio frequency (RF) signals, bioenergy signals, or the like, or any combination thereof. The energy signals may be sensed and received by a receiving device including, for example, an antenna, a solar panel, a thermoelectric device, a piezoelectric device, the like, or any combination thereof. Step 701 may be performed by the antenna 501 (shown in FIG. 5). The system 110 may match the sensed energy signals in step 702. Step 702 may be performed by the matching circuit 502 (as shown in FIG. 5). The matching circuit may be configured as a two-component circuit, an L-matching circuit, a T-matching circuit, a PI-matching circuit, or the like, or any combination thereof. As for the two-component circuit, there may be various variations as illustrated in FIG. 6. The received energy signals may be converted into power signals in step 702. Exemplary power signals may include a DC signal or a voltage signal. In step 703, instructions may be retrieved for power management in order to process the power signals. The instructions may be sent from the power management unit 410 (as shown in FIG. 4). The control signals may cause initializing/restarting energy harvesting, terminating energy harvesting, storing the power signals, providing power for consumption, or the like, or any combination thereof. Afterwards, power relating to the power signals may be stored in step 704 or supplied for consumption in step 705. Alternatively, step 704 and step 705 may be performed simultaneously. In step 704, power relating to the power signals may be stored in one or more energy storing devices including, for example, a battery, a capacitor, super capacitor, or the like, or any combination thereof. The power may be stored so that future operations of the system 110 may be performed using the stored power, without the need to harvest energy. In step 705, the power may be used to power at least some operations of, for example, the system 110 directly.

It should be understood that the above description of the flowchart is provided for illustration purposes, and not intended to limit the scope of the disclosure. For persons having ordinary skills in the art, multiple variations and modifications may be reduced to practice based on the teaching of the present disclosure. However, those variations and modifications do not depart from the scope and spirit of the present disclosure. For example, step 704 and step 705 may be performed sequentially without concerning the specific order; meanwhile, step 703 may be unnecessary and may be skipped.

Figure 8:
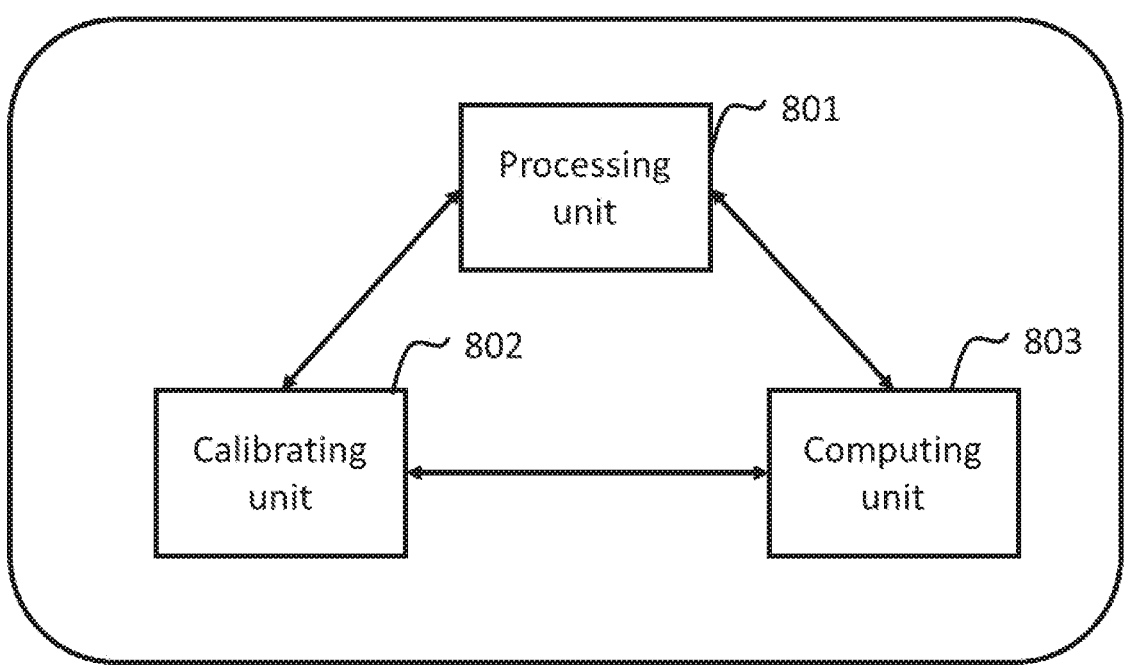
FIG. 8 shows a block diagram of a computing center according to some embodiments of the present disclosure.

FIG. 8 shows an exemplary block diagram illustrating the computing center 304 according to some embodiments of the present disclosure. As shown in the figure, the computing center 304 may include a processing unit 801, a calibrating unit 802, and a computing unit 803. One unit of the computing center 304 may communicate with one or more other units of the computing center 304.

The processing unit 801 may be configured or used to process the information received from the computing unit 803. The information may include the sensory information from an external sensor 130 or an on-board sensor, the control information and command information from an external device 140, the information stored in the memory 303, or the like, or any combination thereof. In some embodiments, the processing unit 801 may provide information to configure some settings of an external sensor 130, for example, a sampling rate, range or accuracy. Furthermore, the processing unit 801 may send the configuration information to one or more other modules of the system 110 including, for example, memory 303, for selecting calibration parameters. The processing unit 801 may send data to the calibrating unit 802 and/or the computing unit 803. The processing unit 801 may output data via the communication module 302, the memory 303, or the energy harvesting module 301. In some embodiments, the processing unit 801 may be configured or used to convert an analog signal to a digital signal when the sensory information from an external sensor 130 is an analog signal. The conversion may be performed by an ADC or other devices. Additionally, the conversion may be implemented based on the control information from an external sensor 130 or an external device 140. Further, the processing unit 801 may be configured or used to generate an initial value for the calibrating unit 802, and the initial value may be sent to the calibrating unit 802. In some embodiments, the processing unit 801 may be configured or used to receive a plurality of batches of sensory information and process the sensory information in a batch mode. The processing unit 801 operating in a batch mode may be configured or used to process the sensory information concurrently or serially.

The calibrating unit 802 may be configured or used to verify the information from the processing unit 801 or the computing unit 803. For example, when the calibrating unit 802 receives an initial value from the processing unit 801, it may produce a calibrated value by processing the initial value and send the calibrated value to the computing unit 803. It should be noted that the calibrated value may be the same as the initial value. The calibrating unit 802 may receive via the communication module 302 information including, for example, a calibration parameter or a calibration formula. The calibration unit 802 may verify the initial value based on the calibration parameter or the calibration formula.

The computing unit 803 may be configured or used to convert the calibrated value or the initial value to a value or format that a user may prefer or understand easily. The computing unit 803 may perform a mapping function for mapping or converting the value to a value that a user may understand. For instance, an electrical signal indicating light intensity, heat intensity, or sound intensity may be mapped or converted to a value that a user may understand. The computing unit 803 may be connected or communication with the processing unit 801 and/or the calibrating unit 802.

The description of the computing center 304 is intended to be illustrative, and not to limit the scope of the present disclosure. Many alternatives, modifications, and variations will be apparent to people having ordinary skills in the art. For example, a storage unit (not shown in FIG. 8) may be added to the computing center 304 for storing pre-processed information, processed information, or the calibrated value. As another example, the processing unit 801 and the calibrating unit 802 may be implemented as a single unit, or the processing unit 801 may be divided into two or more separate units.

FIGS. 9A-9D illustrate exemplary frame formats of different communication protocols. FIG. 9A and FIG. 9B illustrate two different frame formats of International Organization for Standardization (ISO) 15693 protocol. FIG. 9A illustrates a general request format. The request format may include: Start of Frame (SOF), Request Flags, Command Code, Parameters, Data, CRC, and End of Frame (EOF). Frames may be delimited by SOF and EOF, and may be implemented using a code violation. FIG. 9B illustrates a general response format. The response format may include: SOF, Response Flags, Parameters, Data, CRC, and EOF.

FIG. 9C illustrates a standard frame format of ISO 14443 protocol. Standard frames may be used for data exchange and may include Start of communication (S), data, and End of communication (E). The data may be presented in the following formula, n*(8 data bits+odd parity bit), where n≥1. The LSB (Least Significant Bit) of each data byte may be transmitted first. A data byte may be followed by an odd parity bit.

FIG. 9D illustrates a standard frame format of ISO 18092 protocol. Standard frames may be used for data exchange and may include: Start of communication, n*(8 data bits+odd parity bit), where n≥1, and End of communication. The LSB (Least Significant Bit) of each data byte may be transmitted first. A data byte may be followed by an odd parity bit. The parity bit P may be set such that the number of ONEs is odd in (bit 0 to bit 7, P).

Furthermore, the system 110 may provide a function/method for calibrating the information received via, for example, a sensor interface. The calibration may be realized by one or more calibration formulas and/or one or more calibration parameters. The calibration formulas and/or calibration parameters may be stored in a memory of the system 110.

Figure 10:
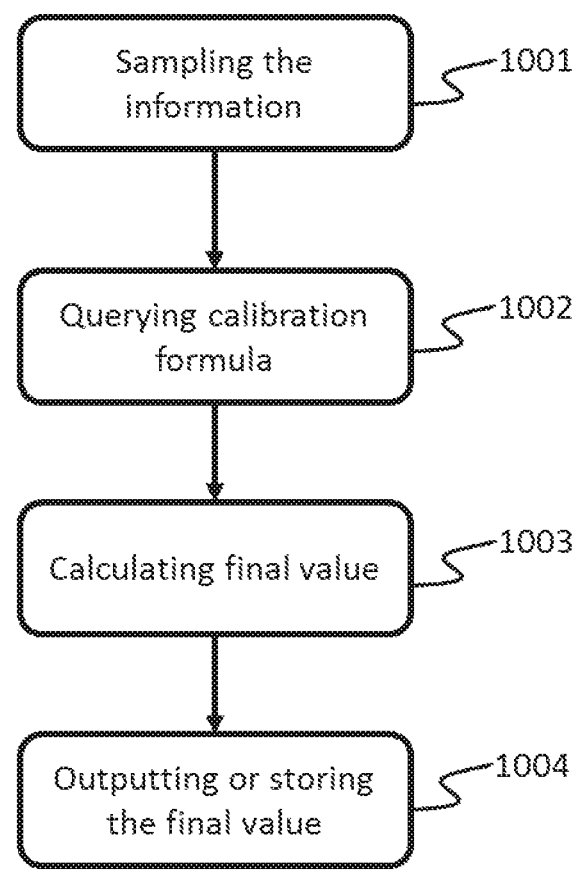
FIG. 10 shows a flowchart of a procedure of processing the information received from the external sensor according to some embodiments of the present disclosure.

An exemplary procedure for processing the information received from an external sensor 130 is shown in FIG. 10. In step 1001, information may be received via, for example, a sensor interface. In some embodiments, at least some of the information received from an analog sensor may be selected and converted to a digital signal. The converted signal may be used as an initial value for calculating a calibrated value. Furthermore, some control information may be received via, for example, the communication module 302. The control information may be used to select the calibration parameters.

In step 1002, one or more calibration formulas or calibration parameters may be selected for the calculation of a calibrated value based on the sampled information or the control information. The calibration formulas may include the Steinhart-Hart equation, the Chebyshev fitting equation, a LUT (Look-Up-Table), an exponential equation, a Fourier equation, a Gaussian equation, an interpolant equation, a power equation, a rational equation, a smoothing spline equation, a sum of sine equation, the Weibul equation, or the like, or any combination thereof. A user may be provided with various calibration formulas to select from. In some embodiments, the user may select which calibration formula(s) to be used. In some embodiments, the selection may be performed based on the type of sensor that is used to provide the information on which calibration is to be performed. The selection of the calibration formula(s) may be performed by setting one or more bits in a register. See, for example, FIG. 17 and the description thereof. The calibration parameter(s) may be selected based on the selected calibration formula(s), the control information, the initial information relating to or measured by, for example, an external sensor or an on-board sensor, or the like, or a combination hereof.

In Step 1003, the calibrated value may be based on the selected calibration formula(s) and/or the calibration parameter(s). The calibration parameter(s) may be determined offline and stored in the system 110, for example, in the storage unit of the system 110. The formats of the calibration parameters for storage may change with the calibration formula(s). The calibrated value may be calculated based on the calibration formula(s), the calibration parameter(s), and the information (for example, information regarding a parameter relating to an object or the ambient environment) from a sensor. The sensor may be an external sensor 130 or an on-board sensor.

In step 1004, the calibrated value may be outputted to, for example, a user or an external device 140. For instance, the calibrated value may be outputted to a visual display device directly so that one or more users may view or manipulate the calibrated value. The calibrated value may be stored in the system 110 so that the calibrated value may be read out when the system 110 is linked to one or more external devices 140.

It should be noted that the flowchart described above is merely provided for the purposes of illustration, and not intended to limit the scope of the present disclosure. Various modifications may be made in the light of the present disclosure. However, the modifications do not depart the scope of the present disclosure. For example, the calibration formula(s) may be utilized when a high precision measurement is performed. In some instances, high precision measurement may be unnecessary. Under this circumstance, steps 1002 and 1003 may be skipped, and step 1004 may be performed directly after step 1001 and the calibrated value may be the same as the initial value.

Figure 11:
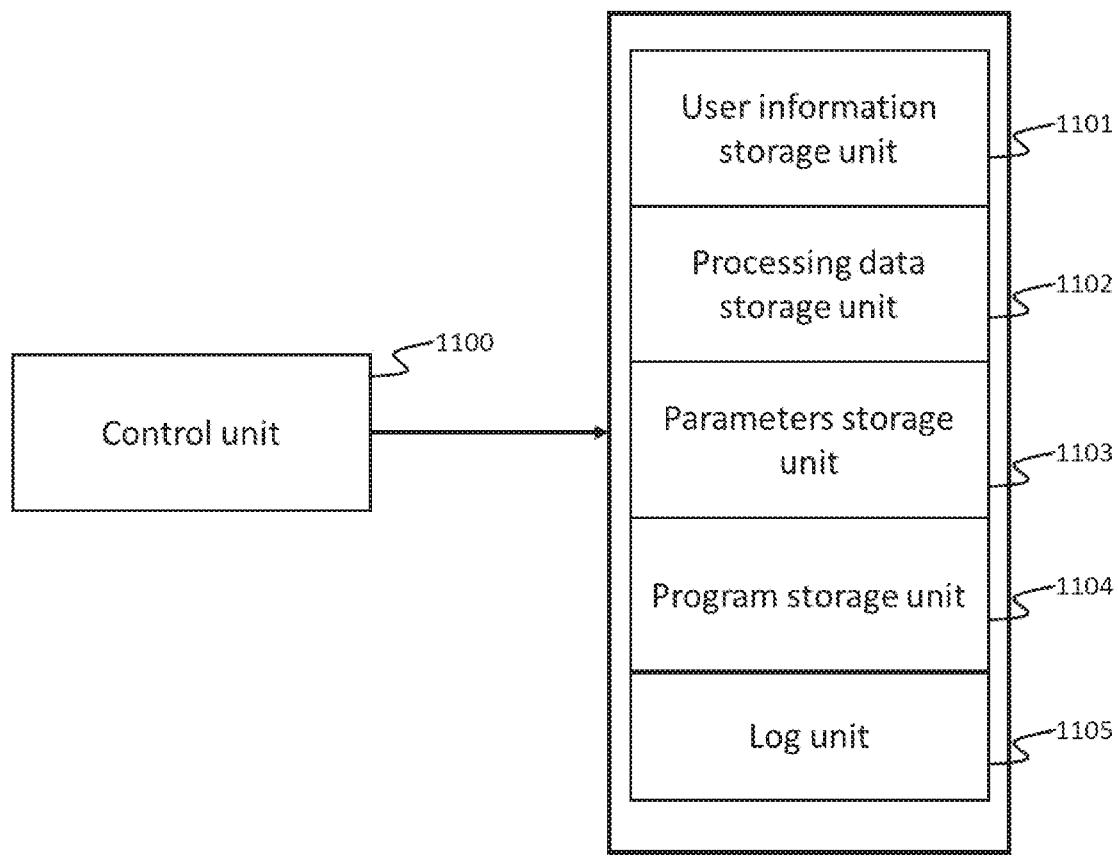
FIG. 11 shows the memory structure in a system according to some embodiments of the present disclosure.

As shown in FIG. 11, the memory in the system 110 may include a user information storage unit 1101, a processing data storage unit 1120, a parameters storage unit 1103, a program storage unit 1104, or the like, or any combination thereof. Furthermore, a control unit 1100 may be configured or used to control access to the storage unit.

The user information storage unit 1101 may be configured or used to store different information that the system 110 may need when it is used in different fields. For example, when the system 110 is used in the medical field, the user information storage unit 1101 may be used to store the information of the measured objects, such as patient identification, the identification of a patient's health care card, a doctor's information, contact information of the patient, of an emergency contact, or of a doctor, the medical history, information regarding the hospital where the patient is treated, information regarding an appointment with a doctor, information regarding a doctor's credentials, medical insurance information, biological characteristics, the identification or manufacturing information of the system that was used to acquire biological characteristics, or the like, or any combination thereof. As another example, if the system has been used in the logistics field, the user information storage unit 1101 may store a coefficient or information of a sensor, the address of a user, the preference of a user, the time when a measurement of a parameter is performed, or the like, or any combination thereof. The user information storage unit 1101 may store, for example, mailing address, contact information, type of delivery, time of delivery, or the like, or any combination thereof.

The processing data storage unit 1120 may store the information that has been processed in the system 110. The information may include information received from a sensor interface, stored information, information from an RF interface, or the like, or any combination thereof. For example, the processing data storage unit 1120 may store the temperature of a human body, PPG, ECG, blood pressure, blood fat, oxyhemoglobin saturation when the system 110 is used in the medical field. As another example, the processing data storage unit 1120 may store information relating to the environment including, for example, temperature, humidity, Particulate Matter 2.5 (PM2.5), radiation, air pressure, or the like, or any combination thereof.

The parameters storage unit 1103 may be configured or used to store parameters that may be used for processing or calibrating information regarding one or more parameters relating to an object or the environment received from, for example, a sensor interface or an RF interface. Exemplary parameters may include the calibration parameters such as the Steinhart-Hart coefficients, the Chebyshev equation coefficients, LUT values, exponential equation coefficients, Fourier equation coefficients, Gaussian equation coefficients, interpolant equation coefficients, power equation coefficients, rational equation coefficients, smoothing spline equation coefficients, sum of sine equation coefficients, Weibul equation coefficients, Fast Fourier Transform (FFT) tables, a cosine or sine table, an average window length, Finite Impulse Response (FIR) coefficients and/or degrees, an offset, or the like, or any combination thereof. Furthermore, exemplary parameters may include other parameters including, for example, physiological coefficients varying with information relating to an individual user.

The program storage unit 1104 may be configured or used to store formulas. Exemplary stored formulas may include calibration formulas or RF communication protocols, etc. The calibration formulas may be used to calibrate the information including, for example, temperature, physical variables, humidity, pulse, pressure, or the like, or any combination thereof. The RF communication protocols may be configured or used to support the communication between the system 110 and an external device 140 or an external sensor 130. The RF communication protocol may include communication protocols, for example, NFC Standard Protocol, RFID Standard protocol, or the like, or any combination thereof.

The log unit 1105 may be configured or used to store redundant information including, for example, a trace log. The trace log may include a trace flag, the sensor identification or characteristics, the monitoring system identification or characteristics, a multimedia message status, error information, a time stamp, a transmission time, the system version, the frequency of data acquisition, the time of data acquisition, or the like, or any combination thereof. The log unit 1105 may be configured or used to package the trace log, add a time stamp and identification information, and then store the trace log. Furthermore, the log unit 1105 may include one or more structures such as a circular buffer to buffer the trace log. The data structure of the log unit 1105 may include a first-in first-out structure, priority queuing, Custom Queuing, Weighted Fair Queuing, Class Based Queuing, Real-time Transport Protocol, or the like, or any combination thereof. The log unit 1105 may be available to a developer, or another type of user. The developer may discover and fix bugs based on the output of the program or debugging information. The user may check some extra information including, for example, a time stamp, error information, the system version, or the like, or any combination thereof.

The control unit 1100 may be configured or used to control access to different types of information stored in the memory or retrieve information (for example, calibration formulas, calibration parameters) stored in the program storage unit 1104. Different users may have different permissions to access the system 110 for reading/writing information. For example, the processing data storage unit 1102 may be set with a first (e.g., the lowest) permission level, and may be accessed when the system 110 is located in close proximity of an external device or when a correct password is provided. The user information storage unit 1101 may be set with a second (e.g., a second lower) permission level. A user who has been granted the access permission may read/write the information stored in the user information storage unit 1101. The parameters storage unit 1103 and/or the program storage unit 1104 may be set with a third (e.g., the most strict) permission level. Only a developer or administrator may access (for example, change, read, or write information) the parameters storage unit 1103 and/or the program storage unit 1104. However, in some embodiments, the developers or administrator may not access the user information storage unit 1101 or the processing data storage unit 1120. The control unit 1100 may be operable to select or retrieve a communication protocols or calibration formulas. Communication protocols may be selected based on, for example, the type of an external sensor 130, the type of an external device 140, the message format in the communication between the system 110 and an external sensor 130 or an external devices 140, or the like, or any combination thereof. The calibration formulas may be selected based on, for example, a user's operation or input, the information received from a sensor interface, the type of the sensor, or the like, or any combination thereof.

The above description is intended to be illustrative, and not to limit the scope of the present disclosure. Many alternatives, modifications, and variations will be apparent to people having ordinary skill in the art. For example, the memory may include a flash, a cache, a buffer, a ROM, a RAM, a register, a Dual In-line Memory Modules (DIMMs), a magnetic disk, an optical disc, a hard disk, a floppy disk, an electron storage, a film memory, a phase change memory, a cloud disk, a NAND flash memory, a NOR flash memory, or the like, or any combination thereof and the RAM may be implemented as one or more of the following types of the memory: static random access memory (SRAM), Burst SRAM or SynchBurst SRAM (BSRAM), dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDECSRAM, PCIOO SDRAM, Double Data Rate SDRAM (DDR SDRAM), Enhanced SDRAM (ESDRAM), SyncLink DRAM (SLDRAM), Direct Rambus DRAM (DRDRAM), Ferroelectric RAM (FRAM), or any other type of memory device. Multiple storage units may be implemented on one memory, or separate memories. As another example, the distribution of the information stored in the memory may appear in a way different from that described above. For instance, biological characteristics or device address may be contained in the parameters storage unit 1103. Similar modifications should fall within the metes and bounds of the claims.

Note that although FIG. 12A-FIG. 12C show three exemplary formats of the calibration parameters stored in, for example, the parameters storage unit 1103, they are provided for illustration purposes. The calibration parameter(s) may be stored in a format other than that shown in these figures. For example, the formats may be based on the Steinhart-Hart equation, the Chebyshev fitting equation, a LUT, an exponential equation, a Fourier equation, a Gaussian equation, an interpolant equation, a power equation, a rational equation, a smoothing spline equation, a sum of sine equation, the Weibul equation, etc. The discussion herein is not limited to any formats of the calibration parameters stored in, for example, the parameter storage unit.

FIG. 12A illustrates an exemplary format of the calibration parameter corresponding to the Steinhart-Hart equation.

The Steinhart-Hart equation as shown in Equation 1 may be used to calculate a calibrated value.

$$T^{-1}=A+B\cdot\ln R+C\cdot(\ln R)^3, \quad \text{Equation 1}$$

where A, B, and C are the Steinhart-Hart coefficients, and R represents the measured resistance. FIG. 12A illustrates an exemplary format of the Steinhart-Hart coefficients stored in, for example, the parameters storage unit 1103. The stored format may be divided to a first part 1201 and a second part 1202. The first part may include a lower limit $\alpha$, an upper limit $\beta$, and a segment-parameter $\gamma$. The lower limit $\alpha$ and the upper limit $\beta$ may define a measurement range of the information received from, for example, a sensor. The segment-parameter $\gamma$ may divide the measurement range into $\gamma$ segments evenly and the measurement range of each segment may be $(\beta-\alpha)/\gamma$. The second part may include $\gamma$ segments. The first segment may be configured or used to store initial coefficients A, B, and C that correspond to the first segment. The remaining segments may be configured or used to store difference values on the basis of the coefficients of the first segment. When the difference values of a segment are positive, the coefficients of the segment are the initial coefficients plus the difference values. Conversely, when the difference values of a segment are negative, the coefficients of the segment are the initial coefficients minus the difference values.

FIG. 12B shows an exemplary format of calibration parameters for the Chebyshev fitting. The Chebyshev equation may be used for calculating the calibrated value according to Equation 2.

$$T = \frac{\alpha_0}{2} + \sum_{i=1}^{n} \alpha_1 \cos(i\cos^{-1} x) \quad \text{Equation 2}$$

where $\alpha_i$ is the coefficient to be solved, and n, the order of Cheyshev equation, may be up to twelve.

As shown in FIG. 12B, the format may include two parts. A first part of the format may include the lower limit $\alpha$ and the upper limit $\beta$. A second part of the format may include an equation order number and equation coefficients.

FIG. 12C shows an exemplary format of the parameters used in a LUT method. When using a LUT method for calibration, an upper limit and a lower limit may be set. The format may include the upper limit, the lower limit, the subsection-parameter, and the resistors value corresponding to each periods into which the field between the upper limit and the lower limit is divided by the subsection-parameter. Aside from the description above, calibration may be performed based on a resistance using an interpolation techniques, for example, linear interpolation or a cubic spline method when the format does not include the resistor value.

In addition to the formats for storing the calibration parameters described herein, the format disclosed herein may also be stored in other storage unit or with other architectures (e.g., different permutation or parts of stored information).

Figure 13:
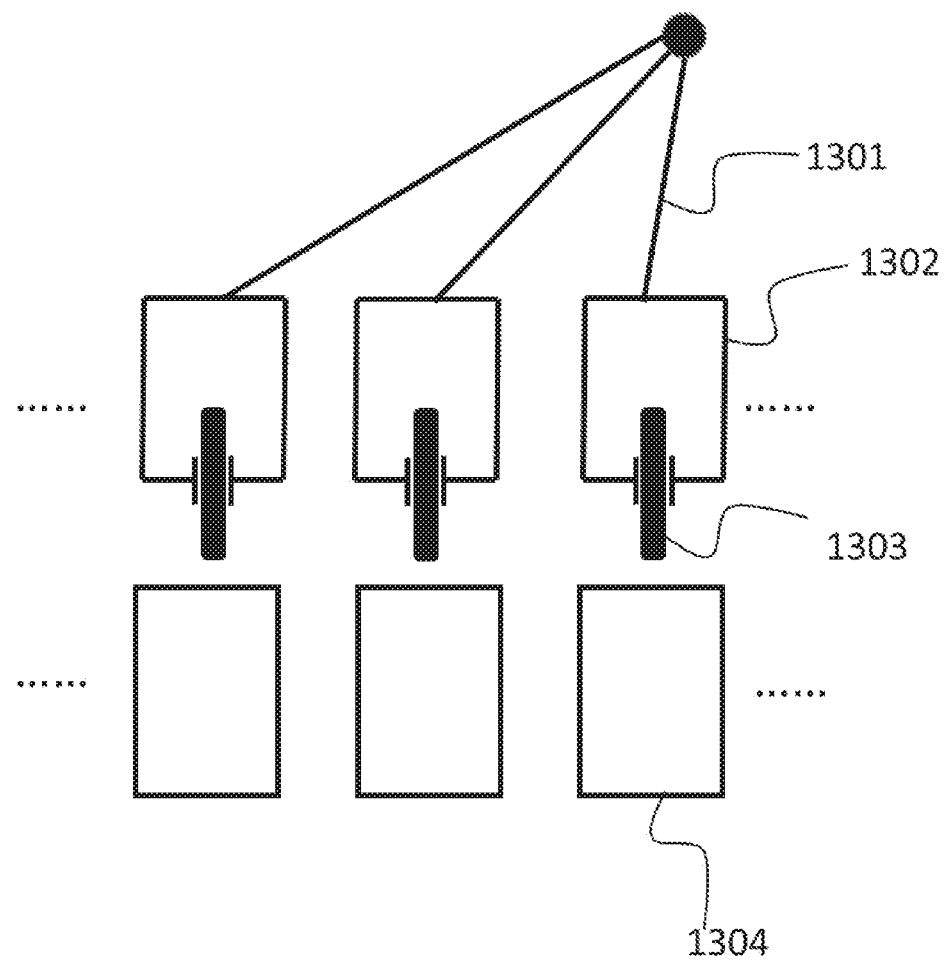
FIG. 13 illustrates an exemplary apparatus for adjusting the calibration parameters used in a system according to some embodiments of the present disclosure.

In order to improve the reliability of the system 110, an apparatus and method for rectifying the calibration parameters are provided. The rectifying of calibration parameters may include testing, judging, and/or adjusting the calibration parameters. FIG. 13 illustrates an exemplary apparatus for testing, judging, and/or adjusting the calibration parameters used in the system 110 according to some embodiments of the present disclosure. The apparatus may include one or more gripper arms 1301, one or more gripper units 1302, and/or one or more thermostatic chambers 1304. The forms of the system 110 may include a measuring chip, a SoC (system of chip) or a patch. The shape of the apparatus may be essentially annular, rectangular, circular, triangular, trapezoidal, quadrate, or the like, or any combination thereof.

Merely by way of example, a gripper unit 1302 may be configured or used to hold a measuring chip 1303 in the thermostatic chamber 1304 for rectification. The gripper unit 1302 may be connected to a gripper arm 1301 so as to be movable in a plane or in a space to thereby move the held measuring chip 1303 according to a predetermined procedure. The measuring chip 1303 may include other forms, for example, a patch, a capsule, etc. The thermostatic chamber 1304 may be configured or used to contain the measuring chip 1303 and keep the measuring chip 1303 at a predetermined temperature. The number of the thermostatic chamber 1304 may be determined in accordance with the requirements of precision and the plant area.

The apparatus may be configured or used to calculate the calibration parameters and judge rationality of the calibration parameters. Firstly, the gripper unit 1302 may hold one or more measuring chips 1303 and the gripper arms 1301 may move and put the measuring chips 1303 in the thermostatic chamber 1304. Then, in a rectification procedure, the apparatus may obtain a resistance in accordance with the predetermined temperature after the measuring chips 1303 have reached a steady state in terms of the temperature measurement. Finally, the gripper arm 1301 may be moved to change the relative position between the measuring chips 1303 and the thermostatic chambers 1304, and repeat the above rectification procedure. The apparatus may obtain another resistance in accordance with another predetermined temperature. The above rectify procedure may be repeated N times if the calibration formula to be rectified has N coefficients to be determined. Then each measuring chip may get a series of resistance to temperature (R-T) table that relates to at least some characteristics of the measuring chip. Exemplary characteristics may include Media Access Control (MAC) address, User Identifier (UID), etc. The apparatus may be configured or used to calculate unknown calibration parameter(s) based on the R-T table.

After the coefficients have been determined, the rectification procedure may be repeated for additional times for judging whether the calibration parameters are reasonable. One or more additional R-T tables acquired in the further rectification procedure may be used to calculate a temperature $T_c$ corresponding with a $T_m$ which may be computed based on the determined calibration parameters. If $|T_c-T_m|<e$, where e is the minimum allowable error, the calibration parameters in the measuring chip may be regarded as reasonable. Otherwise, the calibration parameters may be regarded as unreasonable and may be calculated again based on the additional R-T table(s) and the original R-T table.

It should be noted that the description of the diagram is provided for illustration purposes. For persons having ordinary skills in the art, adjustments and modifications may be made without departing from the principle or spirit of the present disclosure. Therefore, it is given that the present disclosure should not be limited by the specific description herein. For example, one measuring chip 1303 may be immersed in a thermostatic chamber 1304 at a time for rectifying a LUT calibration formula. As another example, the measuring chip 1303 may be immersed in a number of thermostatic chambers 1304, where the number may be determined based on the number of the unknown coefficients in, for example, the Steinhart-Hart equation or the Chebyshev equation. Such alternatives, modifications, and variations will also be within the scope of this disclosure.

Figure 14:
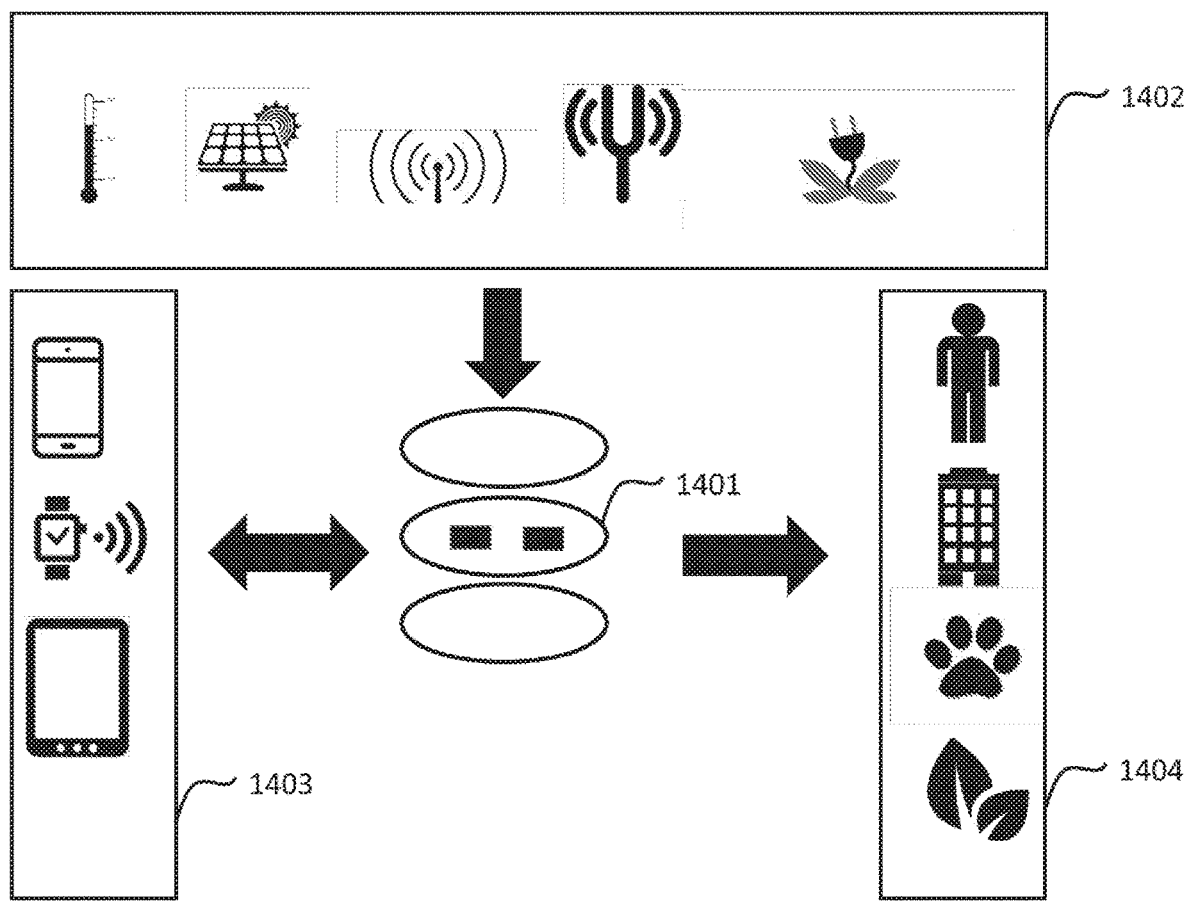
FIG. 14 depicts a schematic diagram of a system according to some embodiments of the present disclosure.

FIG. 14 depicts a diagram of the system 110 according to some embodiments of the present disclosure. The system 110 may be implemented as a patch 1401 as shown in the figure. The patch 1401 may be configured or used to receive temperature value from various temperature sensors by providing corresponding sensor interfaces. Such temperature sensors may be manufactured by different companies with corresponding sensor interfaces. After the temperature value is acquired, a calibration process may be performed based on the acquired temperature value to generate a calibrated temperature value. The calibrated temperature value may be stored in a desired area of the patch 1401. The patch 1401 may communicate with one or more external devices 1403. The patch 1401 may include a flexible material including, for example, polyethylene (PE), spandex, cloth, Polyvinyl chloride (PVC), non-woven fabric, Polyurethane (PU), or the like, or any combination thereof. The patch 1401 may include an adhesive to facilitate its attachment to a surface of an object. At least a portion of the patch 1401 may be waterproof.

The patch 1401 may harvest energy from, for example, energy sources 1402, in the ambient environment. Exemplary energy sources 1402 may include thermal energy, solar energy, RF energy, vibration energy, bioenergy, or the like, or any combination thereof. The patch 1401 may be attached to a target object 1404. The target object 1404 may include a human body, a building, an animals, a plants, or the like, or any combination thereof.

In some embodiments of the present disclosure, the patch 1401 may be attached to a human body for monitoring the body temperature. The patch 1401 may have a built-in temperature sensor that may be configured or used to measure the temperature of the body. Alternatively, the patch 1401 may be connected to or communicate with an external temperature sensor that may be attached on the human body or may measure the body temperature in another means. The patch 1401 may be attached to the neck, an arm, a leg, a knee, the head, a finger, the back, the chest, a foot, or the like, or a combination thereof. The patch 1401 may continuously or intermittently monitor the temperature of the body. The temperature value may be acquired by the patch 1401, calibrated, and stored in a desired area or portion of the patch 1401. It should be noted that the calibrated temperature value may be encrypted utilizing one or more encryption algorithms. When a reading operation is performed on the patch 1401, an external device 1403 (for example, a smart phone) may retrieve the calibrated temperature values from the patch 1401.

The communication between the external device 1403 and the patch 1401 may be achieved via a wired connection or wirelessly. Exemplary external devices 1403 may include a smart phone, a smart watch, a tablet, a smart band, a personal computer (PC), a game box, a laptop, a personal digital assistant (PDA), or the like, or any combination thereof. For example, the patch 1401 may be connected with a PC or a laptop via a cable and the calibrated temperature value may be sent through the cable to the PC or the laptop. As another example, the patch 1401 may send the calibrated temperature value to the external devices 1403 by the application of one or more wireless communication protocol including, for example, near field communication (NFC), radio-frequency identification (RFID), or a combination thereof.

If it is the first time the external device 1403 communicate with the patch 1401, a matching or pairing operation may be performed. With an application of international mobile equipment identity (IMEI), serial number (SN), media access control (MAC), or the like, or any combination thereof, the external device 1403 (for example, a smart phone) may be paired with the patch 1401. After the pairing is established, the patch 1401 may transmit the calibrated temperature value to the external device 1403. Apart from the pairing operation described above, a password protection mechanism may be added into the patch 1401. That is, when a pairing operation is performed, the user of the external device 1403 may be asked to provide a password to pair the external device 1403 with the patch 1401 and retrieve the calibrated temperature values stored therein. In some embodiments, once the pairing of the external device 1403 and the patch 1401 has been successfully performed, subsequent pairing may be performed automatically without the need to provide the password. In some embodiments, a user may need to provide a password for each time a pairing operation is performed.

The external device 1403 may be equipped with an application-specific software for processing the calibrated temperature values. For instance, the software may produce a temperature curve for a specific period including, for example, an hour, a minute, a day, a week, a month, a year, a season, or the like, or any combination thereof. The period may be preset by a manufacturer, and may be adjusted by a user afterwards. Furthermore, the software may generate a time tag when a calibrated temperature value is retrieved. An electronic medical system may be employed to analyze the calibrated temperature values.

In some embodiments of the present disclosure, the system 110 may be implemented as a smart capsule with an organic cover. The smart capsule may have a built-in micro-camera that may be utilized for medical diagnosis after the capsule is administered to a patient. For instance, the smart capsule may be used for gastrointestinal diagnosis. The cover of the smart capsule may degrade in the presence of gastric acid when the smart capsule arrives at the stomach of the patient. Meanwhile, energy may be produced as the cover degrades. The smart capsule may be powered by the energy released from the degradation of the cover, and may take images of the gastric cavity. One or more receiving terminals may be configured or used to receive images transmitted by the built-in micro-camera inside the smart capsule. The smart capsule may be distributed with surface without causing damages to human bodies.

In some embodiments of the present disclosure, one or more patches 1401 may be placed in a building for the purpose of monitoring indoor temperature. A plurality of patches 1401 may be distributed in the building, for example, at least one patch for a room. The patches in the building may be connected to form a sensor network. Each patch may have a unique identification for the recognition of the its characteristics including, for example, its position. Thus, the temperature of a room in the building may be monitored. Merely by way of example, such information may be used to advise how to adjust the temperature or the air conditioning system in the building.

It should be noted that the descriptions herein is provided for purposes of understanding the disclosure, and not intended to limit the scope of the present disclosure. For persons having ordinary skills in the art, various variations and modifications may be performed with a reasonable understanding of the present disclosure. However, those variations and modifications may not depart the spirit and scope of the present disclosure. For example, the patch 1401 may be applied with a smart skin.

Figure 15:
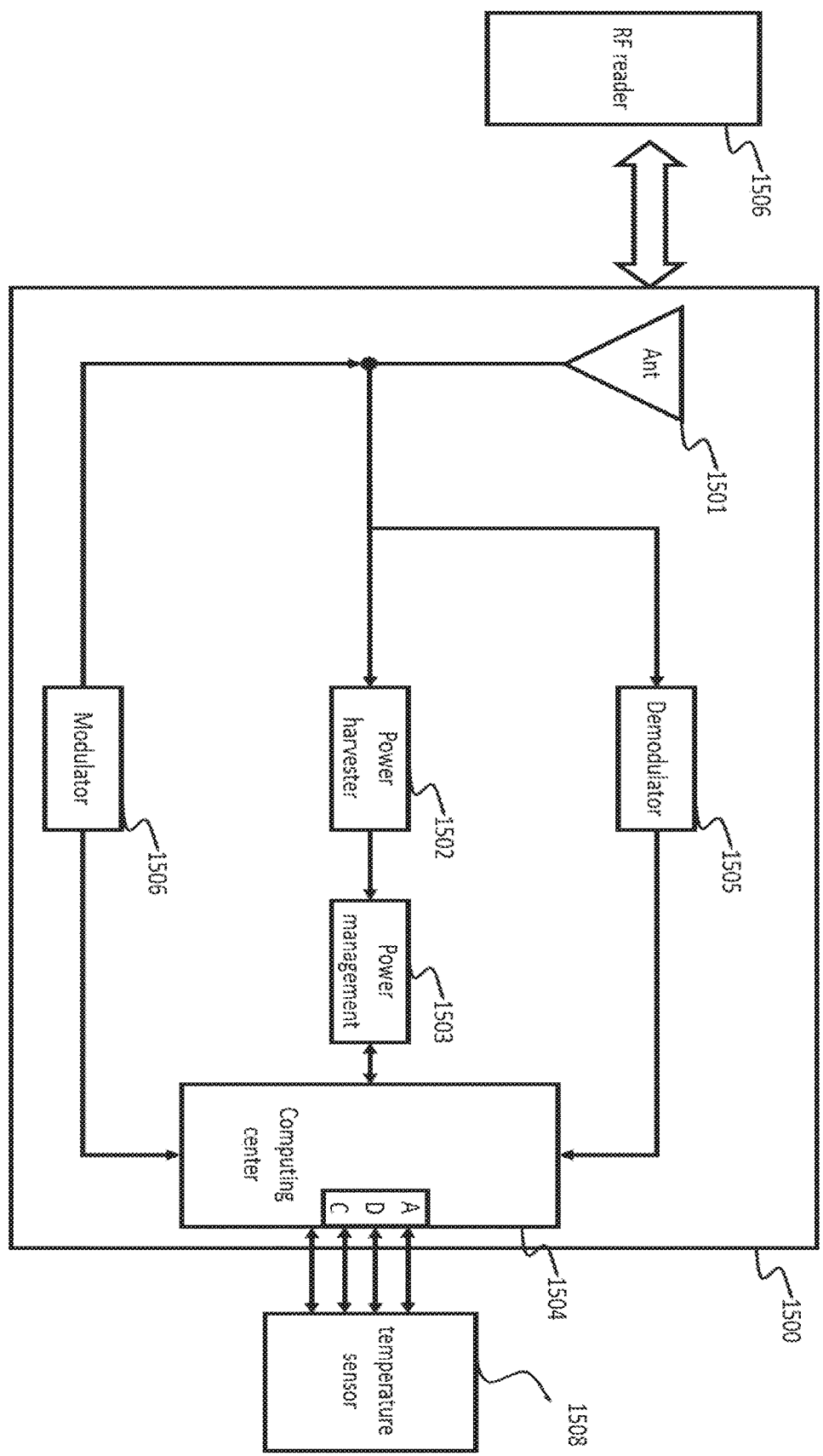
FIG. 15 depicts a block diagram of a system according to some embodiments of the present disclosure.

FIG. 15 shows an exemplary block diagram of a measuring chip 1500 according to some embodiments of the present disclosure. An antenna 1501 may be configured or used to receive information from an RF reader 1507. The antenna may also be configured or used to receive energy from the ambient environment and transfer the energy to a power harvester 1502 for harvesting energy.

The power harvester 1502 may be configured or used to convert the incoming energy into power in the form of, for example, DC voltage, to power the chip or be stored. The power management 1503 may be configured or used to monitor power connections and battery charges, control power delivered to other parts of the chip, manage the interfaces of the measuring chip, regulate the real-time clock (RTC), control sleep or other power functions, or the like, or any combination thereof.

The demodulator 1505 may follow the envelope of the RF carrier wave received by the antenna 1501 to extract useful data streams. This extracted baseband waveform may be processed by the computing center 1504 to retrieve downline data from the external device, for example, the RF reader 1507.

The computing center 1504 may be configured or used to process the extracted baseband waveform and generate an uplink data stream. The uplink stream data may be sent via the modulator 1506 and the antenna 1501 to the RF reader 1507, or some other external devices.

Furthermore, the temperature sensor 1508 may be connected to the computing center 1504 via, for example, one or more of adhesive, a clip, a blinding, a tape, etc. The temperature sensor 1508 may be electrically and/or thermally connected to the measuring chip 1500 via, e.g., a wire, a wireless connection, a thermocouple, etc. The temperature sensor 1508 may include one or more thermocouple, Resistance Temperature Detector (RTD), Positive Temperature Coefficient (PTC), or a Negative Temperature Coefficient (NTC), or the like, or any combination thereof. The information from the temperature sensor 1508 may be received by the computing center 1504 and converted to digital information via an ADC when the external sensor is an analog sensor. The temperature sensor 1508, which may be an on-board sensor, may be powered by the harvested power.

Figures 16, 17:
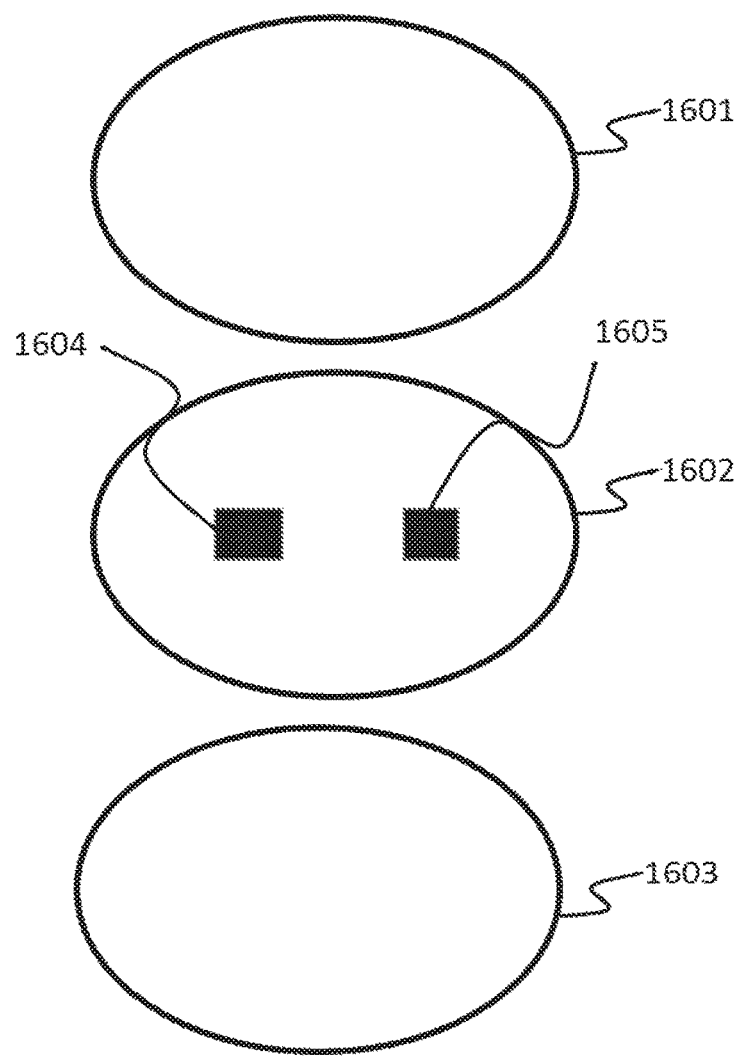
FIG. 16 shows a structure of a patch according to some embodiments of the present disclosure.
FIG. 17 illustrates a structural diagram of a register for controlling the memory of a system according to some embodiments of the present disclosure.

FIG. 16 shows an exemplary structure of the patch 1401 according to some embodiments of the present disclosure. As shown in FIG. 16, the patch 1401 may include an upper layer 1601, an intermediate layer 1602, a lower layer 1603, an antenna contact 1604, and a measuring chip 1605 attached on the intermediate layer 1602. The upper layer 1601 may include a film or a flexible material. The film may be made of polyethylene (PE), spandex, cloth, Polyvinyl chloride (PVC), non-woven fabric, Polyurethane (PU), or the like, or any combination thereof. The upper layer 1601 may be waterproof.

The intermediate layer 1602 may be configured or be used to measure, and/or inputting/outputting information. The antenna contact 1604 may be configured or used to connect with an antenna, receive information or energy from the ambient environment, or send information of a measuring chip 1605 to an external devices. The antenna may be a flexible antenna that may allow the shape of the patch to be adjusted. The measuring chip 1605 may be configured or used to measure and verify the information such as temperature, and provide an output through a selected communication protocol. The lower layer 1603 may include an adhesive material such as an adhesive fabric for attaching the patch 1401 to a surfaces of an object.

FIG. 17 illustrates a structural diagram of a register according to some embodiments of the present disclosure. The register may be utilized to control the memory of a measuring chip/system. As shown in the figure, the register 1701 is an 8-bit register and C0 is the least significant bit. C0 and C1 may be configured or used to identify a calibration mode. The calibration mode may include the Steinhart-Hart equation, the Chebyshev fitting equation, a LUT (Look-Up-Table), an exponential equation, a Fourier equation, a Gaussian equation, an interpolant equation, a power equation, a rational equation, a smoothing spline equation, a sum of sine equation, the Weibul equation, or the like, or any combination thereof. The specific number for a calibration mode is configurable. For example, if C1 and C0 are set as 00, 01 or 10, it may indicate that the selected calibration mode may be LUT, the Steinhart-Hart equation, or the Chebyshev fitting equation, respectively. Bit REF may be configured or used to control whether to apply an ADC offset. Bit TYPE may be configured or used to control the interface setting including, for example, whether an analog sensor temperature or a digital temperature sensor is used. Bit AVG may be configured to indicate whether to use a mean filter. The remaining 3 bits may be reserved for further configuration. For example, the remaining 3 bits may be utilized to store an offset voltage when the ADC offset is open, store a sampling frequency, or a window period of the mean filter, etc. Alternatively, three different registers may be utilized to configure the offset voltage, the sampling period, and the window period, respectively.

It will be understood that the configuration of the register in FIG. 17 is exemplary and may vary. The above described function of the register may not be restricted by the number and position of the bits in the register. The register may be located in the computing center 304 or the memory 303.

Figure 18:
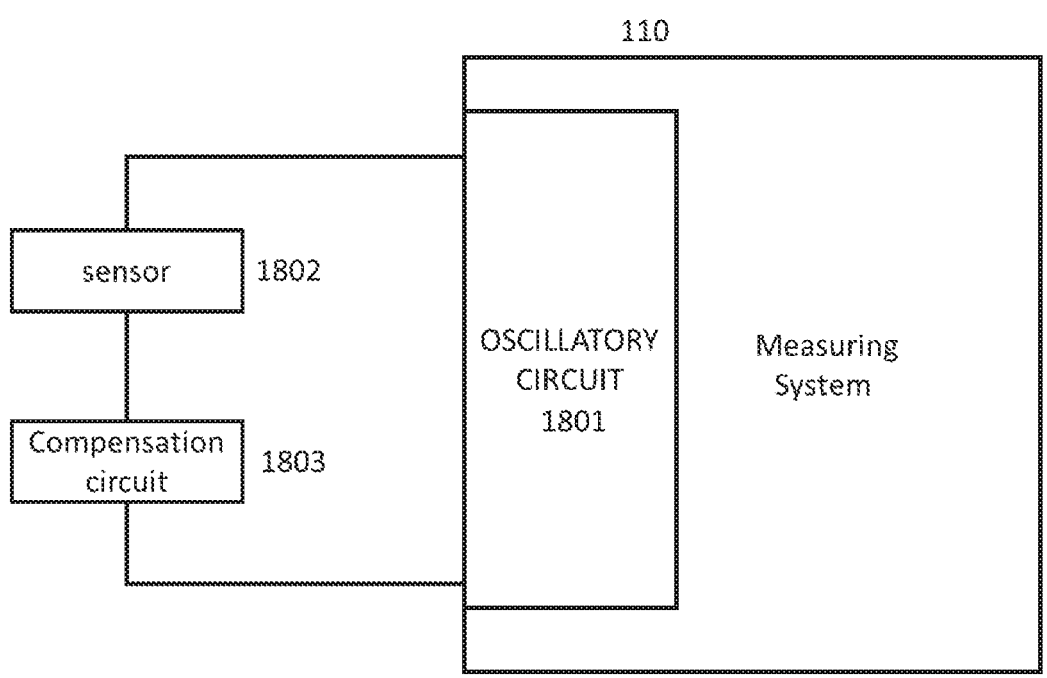
FIG. 18 illustrates a diagram of an oscillatory circuit according to the present disclosure.

FIG. 18 illustrates an exemplary diagram of the system 110 using an oscillatory circuit according to the present disclosure. The system 110 may be configured or used to be integrated with one or more oscillatory circuits 1801. The oscillatory circuit 1801 may be coupled to one or more compensation circuits 1803 and one or more sensors 1802. The oscillatory circuit 1801 may be one of the circuits shown in FIGS. 19, 20, 21, 22, and 23. The sensor 1803 may include at least one thermistor having a resistance varying with temperature, for example, a Positive Temperature Coefficient (PTC), or a Negative Temperature Coefficient (NTC) thermistor. The compensation circuit 1803 may include a parallel series circuit of at least one compensation resistor having, for example, a fixed resistance, and at least a fixed capacitor.

Furthermore, the oscillatory circuit 1801 alone may perform compensation. The combination of the oscillatory circuit 1801 and the compensation circuit 1803 may provide a further compensating effect.

Figure 19:
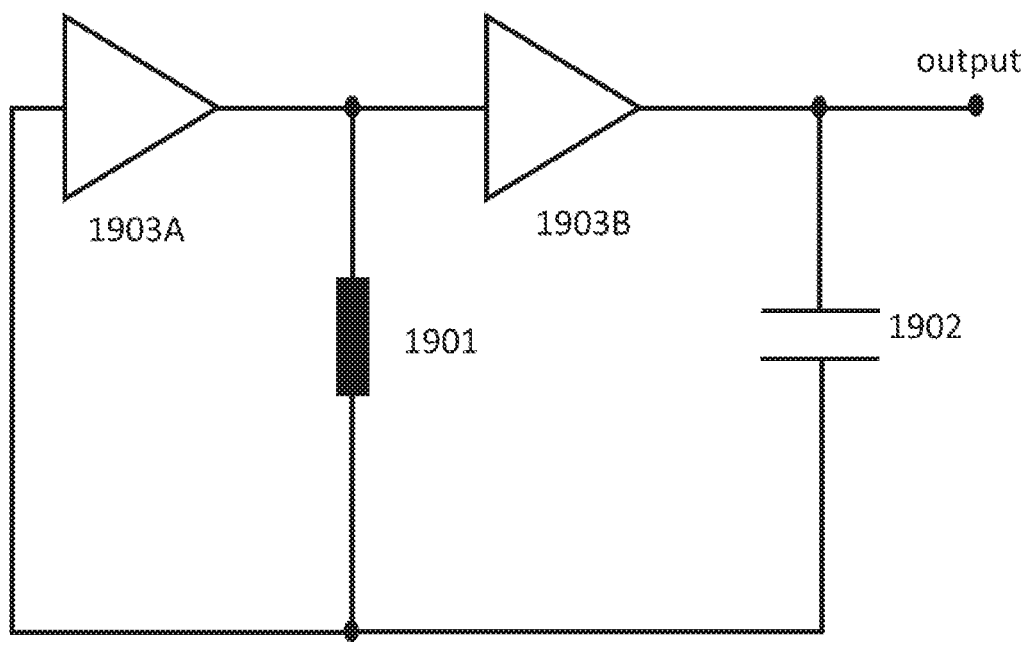
FIG. 19 illustrates an example of the oscillatory circuit according to some embodiments of the present disclosure.

FIG. 19 illustrates an example of the oscillatory circuit according to some embodiments of the present disclosure. As shown in FIG. 19, the oscillatory circuit may include a thermistor 1901, a capacitor 1902, and two CMOS Hex Inverters 1903A and 1903B. The oscillatory circuit may be configured or used to provide a frequency signal relating to a measured temperature.

The circuit of the example shown in FIG. 19 may be described by Equation 3:

$$f = \frac{1}{2\pi\sqrt{RC}}, \quad \text{Equation 3}$$

where f is the frequency of the output, R is the resistance of the thermistor 1901, and C is the fixed capacitance of the capacitor 1902.

The resistance of the thermistor 1901 may be calculated using Equation 3 in the case that the system 110 may obtain the frequency of the output. Then, the measured temperature may be obtained through the relationship between the resistance of thermistor and temperature.

Figure 20:
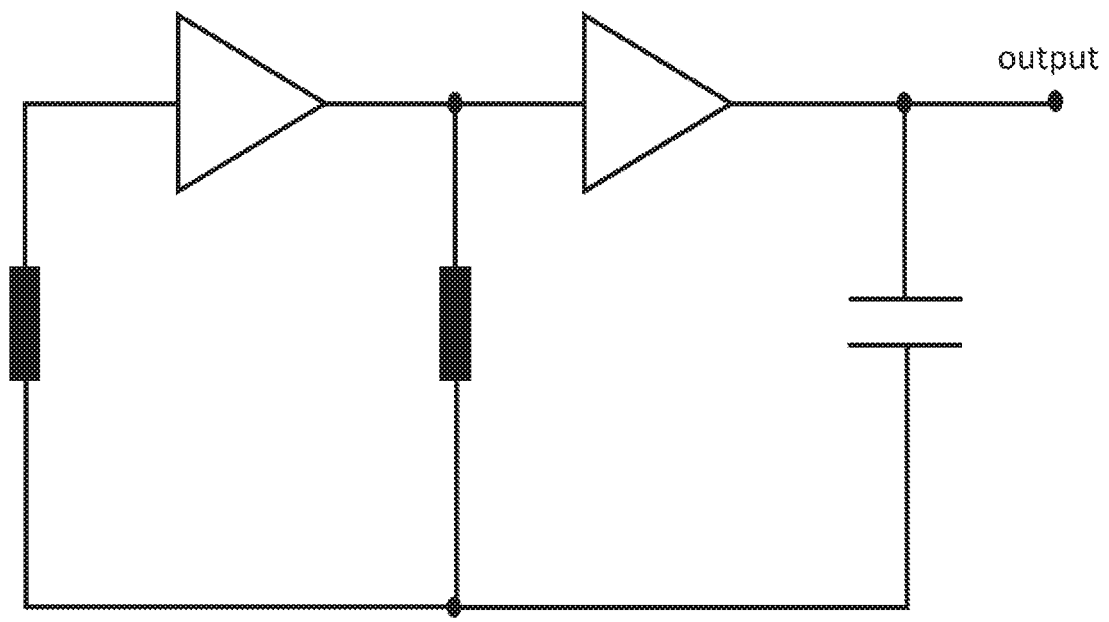
FIG. 20 is another example of an oscillatory circuit according to some embodiments of the present disclosure.

FIG. 20 is another example of an oscillatory circuit according to some embodiments of the present disclosure. When compared with the example illustrated in FIG. 19, the circuit shown in FIG. 20 may add a compensation resistor so that the circuit may be more stable.

Figure 21:
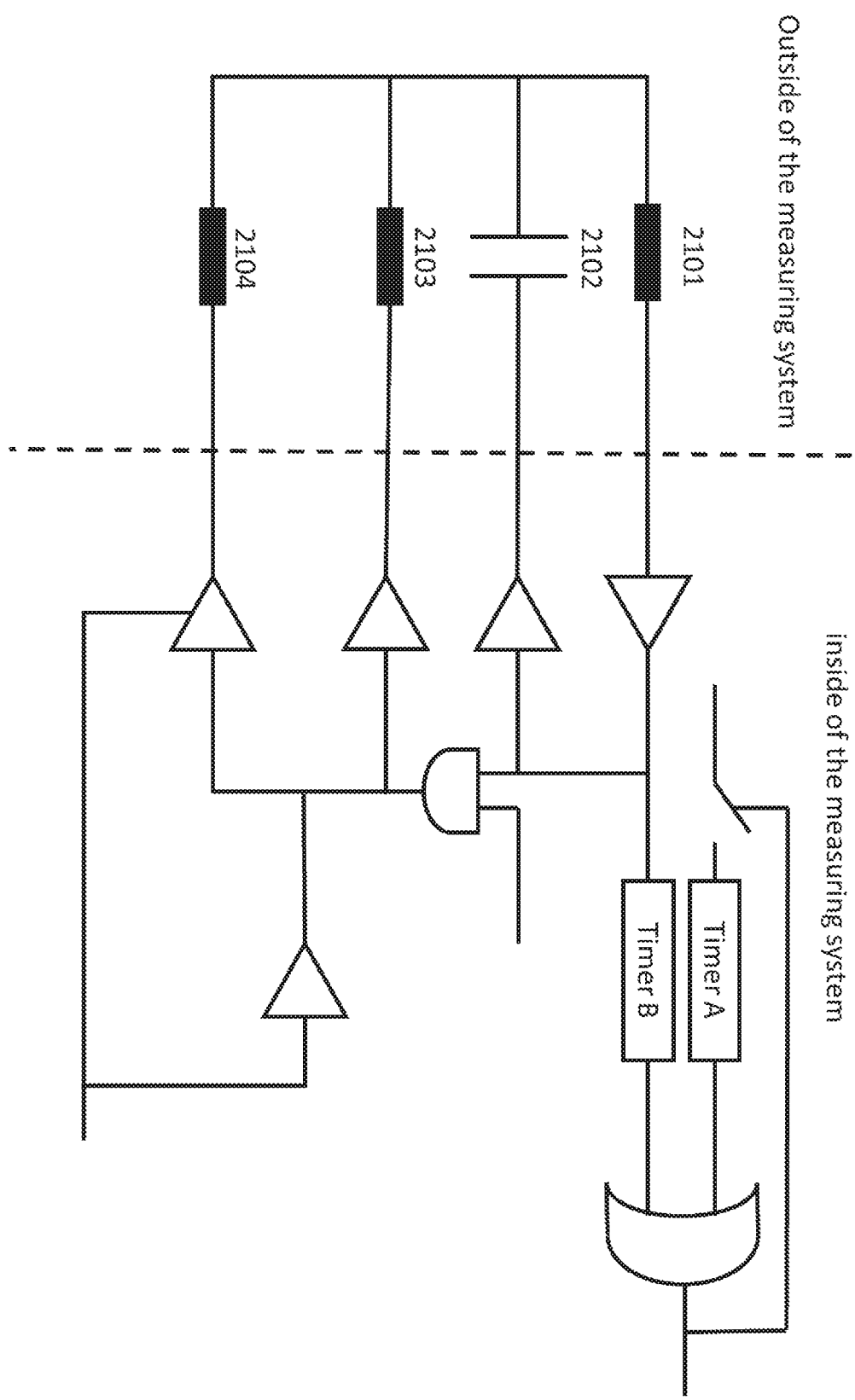
FIG. 21 illustrates another example of an oscillatory circuit according to some embodiments of the present disclosure.

FIG. 21 illustrates another example of an oscillatory circuit according to some embodiments of the present disclosure. The oscillatory circuit may be divided to two parts, one of which may be integrated in the system 110, the other may be connected with the first part of the oscillatory circuit. The outside of the system 110 may include a reference resister 2101, a capacitor 2102, a thermistor 2103, and/or a compensation resistor 2104. The resistance of the reference resister 2101 may be known before a measurement. The oscillation frequency $F_1$ of the oscillation circuit generated by the combination of the reference resistor 2101, the capacitor 2102, and/or the compensation resistor 2104 may be calculated firstly in a measurement procedure. Then the oscillation frequency $F_2$ of the oscillatory circuit generated by the combination of the capacitor 2102, the thermistor 2103 and/or the compensation resistor 2104 may be calculated. Next, the resistance of the thermistor 2103 may be calculated based on Equation 4.

$$\frac{F_1^2}{F_2^2} = \frac{R_o}{R_f}, \quad \text{Equation 4}$$

where $R_o$ may be the resistance of the thermistor 2103, and $R_f$ may be the resistance of the reference resistor 2101.

Then the resistance of the thermistor may be calculated according to Equation 5:

$$R_o = \frac{F_1^2}{F_2^2} * R_f, \qquad \text{Equation 5}$$

When the resistance is determined, the system 110 may be configured or used to calculate the temperature based on the relationship between the resistance of the thermistor and temperature.

Figure 22:
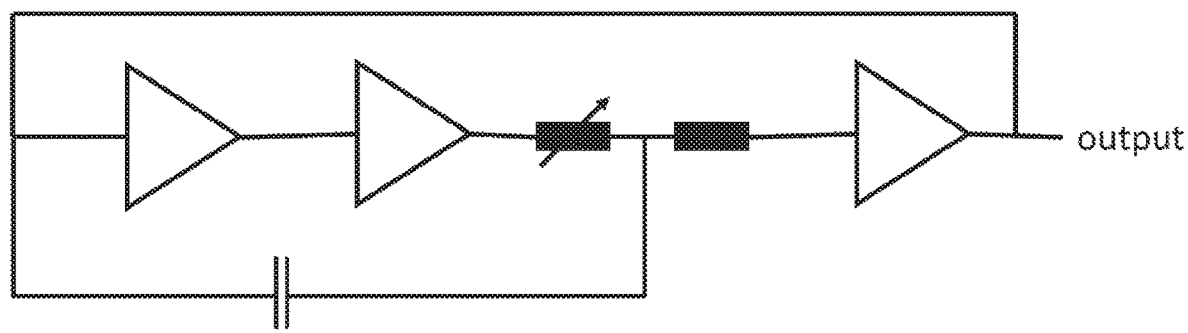
FIG. 22 shows a circuit of the Ring oscillator according to some embodiments of the present disclosure.
Figure 23:
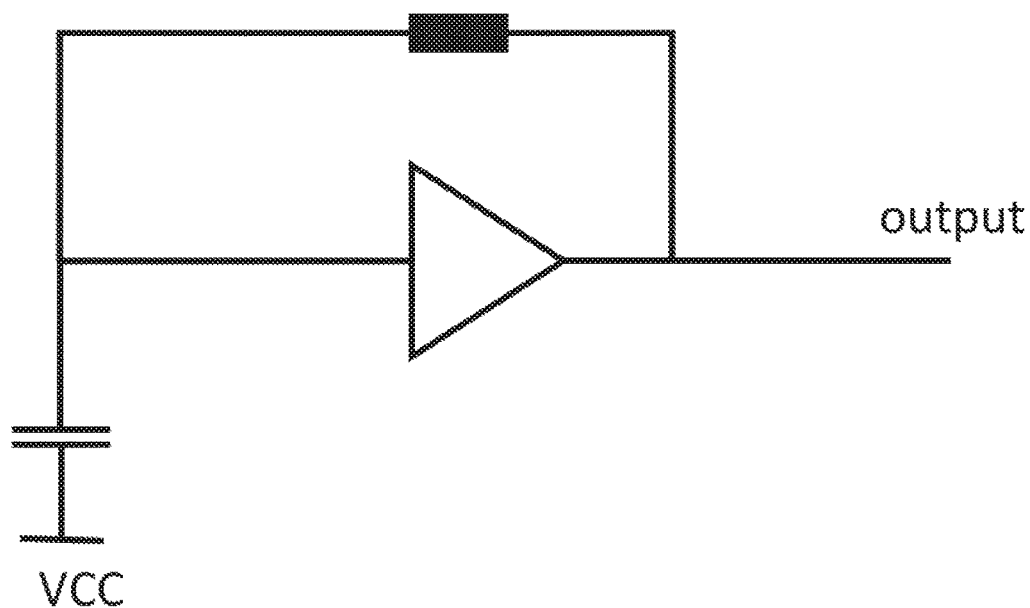
FIG. 23 shows a circuit of the Schmidt trigger oscillator according to some embodiments of the present disclosure.

FIG. 22 shows an exemplary circuit of the Ring oscillator according to some embodiments of the present disclosure. FIG. 23 shows an exemplary circuit of the Schmidt trigger oscillator according to some embodiments of the present disclosure. The circuits shown in FIGS. 22 and 23 may include one or more thermistors, one or more inverters, one or more fixed resistors, and one or more capacitors. The circuits may be configured or used to output a signal with a frequency relating to the temperature measured by the thermistors.

It should be noted that the description of the diagram is provided for illustration purposes. For persons having ordinary skills in the art, adjustments and modifications may be made without departing from the principle or spirit of the present disclosure. Therefore, it is given that the present disclosure should not be limited by the specific description herein. For example, the reference resistor 2101 may be integrated in the system shown in FIG. 21 and the oscillatory circuit may be replaced by other oscillatory circuit, for example, Wien bridge oscillator, oscillator composed of 555 timer, Positive feedback oscillation circuit. As another example, the thermistor 2103 may provide an output proportional to the duty cycle of the signal in order to achieve the specified sensor accuracy. Such alternatives, modifications, and variations will also be in the scope of this disclosure.

Figure 24:
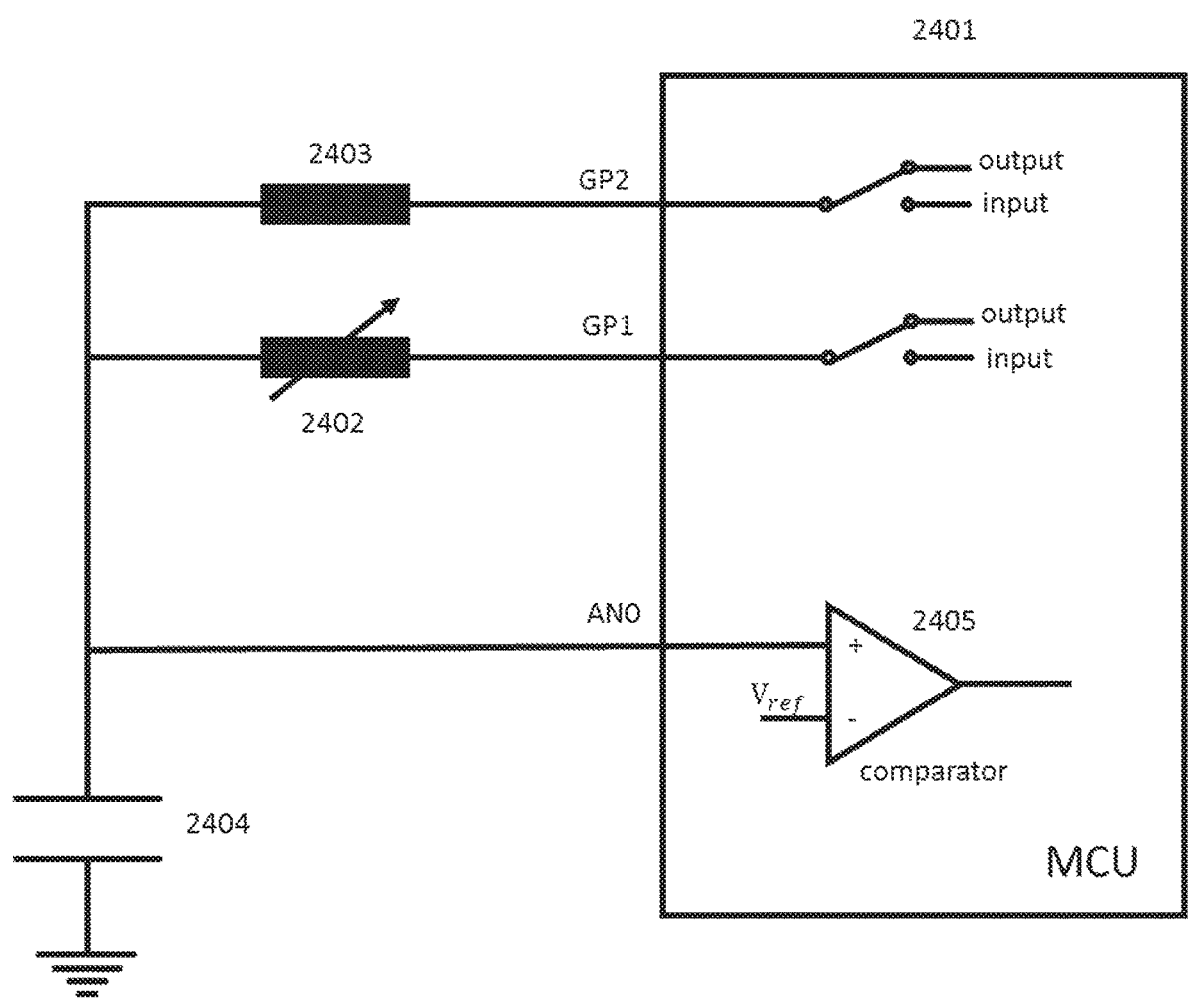
FIG. 24 shows a circuit for calculating resistance of thermistor using RC timing method according to some embodiments of the present disclosure.

FIG. 24 shows a circuit for calculating resistance of thermistor using RC timing method according to the present disclosure. As shown in the figure, the circuit may include a Microcontroller Unit (MCU) 2401, a thermistor 2402, a reference resistor 2403, and a capacitor 2404. The thermistor 2402 may have a variable resistance $R_s$ whose resistance may depend on the temperature. The reference resistor 2403 and the capacitor 2404 may have a fixed resistance $R_0$ and a fixed capacitance $C_0$, respectively. The MCU 2401 may include a comparator 2405 coupled to a Pin AN0 and a reference voltage $V_{ref}$, which may be provided by the internal circuit or the external voltage. The MCU 2401 may further include two Pins GP1 and GP2. The Pins AN0, GP1, and GP2 may be configured to be connected with RC combination circuit composed of thermistor 2402, reference resistor 2403, and capacitor 2404.

The described circuit may be configured or used to calculate the resistance of the thermistor 2402 based on the different time of discharging or charging the capacitor to a specific voltage between the thermistor 2042 and the reference resistor 2403. When voltage is applied to the RC combination circuit for charging the capacitor 2404 or the capacitor 2404 has been fully charged and starts to discharge, the capacitor's voltage may increase or decrease exponentially and the ramping time may be measured with the comparator 2405. The resistance of the thermistor 2402 may be calculated by comparing the ramp rates of the thermistor 2402 and the reference resistor 2403.

Merely by way of example, when the capacitor 2404 is charged, the ramping time measurement may begin by configuring the Pin GP1 as a logic '1' output and GP2 as an input. This may connect the thermistor 2402 to a logic-high voltage, while the reference resistor may be disconnected from the circuit via the high impedance of an input pin. The pin AN0 may be configured as an input and connect the capacitor to the comparator 2405 inside the MCU 2401. The time needed for the capacitor voltage to ramp-up to the reference voltage $V_{ref}$ of the comparator 2405 may be determined through either a hardware or software timer (not shown in the figure). Once the measurement is completed, the GP1 pin may be toggled to a logic '0' output to discharge the capacitor. The configuration procedure of GP1 and GP2 may be then reversed in order to measure the reference resistor 2403. The configuration procedure may be also be used to measure the ramping time when the capacitor 2404 is discharged.

Figure 25:
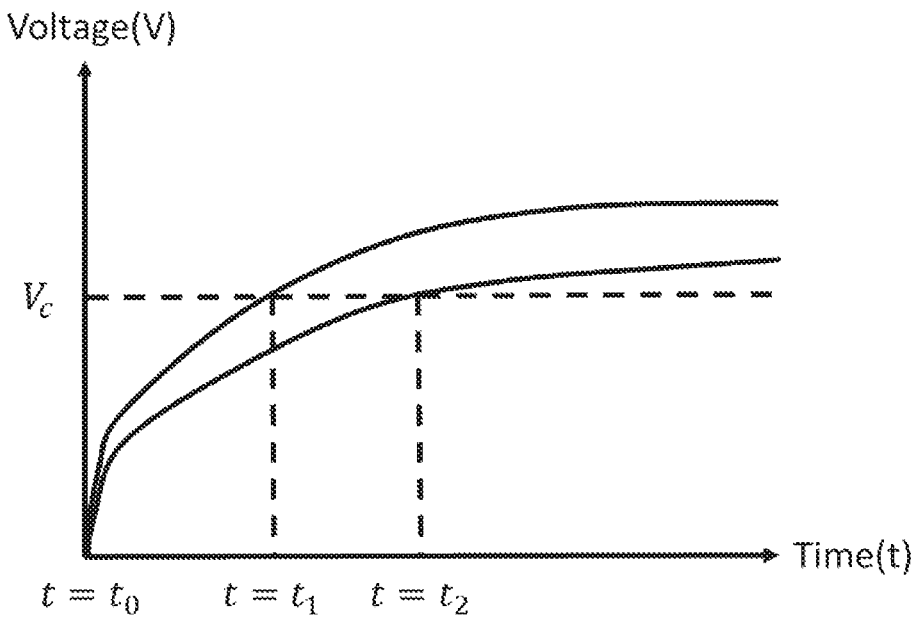
FIG. 25 shows the increase of the charged capacitor's voltage according to some embodiments of the present disclosure.

FIG. 25 shows the increase of the charged capacitor's voltage according to the present disclosure. The resistance $R_S$ of the thermistor 2402 may be calculated based on Equations 6, 7 and 8:

$$V_C = V_{DD}\left(1 - e^{\frac{-t}{RC}}\right), \qquad \text{Equation 6}$$

$$t = -RC * \ln\left(1 - \frac{V_C}{V_{DD}}\right), \text{ and} \qquad \text{Equation 7}$$

$$R_s = \left(\frac{t_2}{t_1}\right)R_{ref}, \qquad \text{Equation 8}$$

where $V_{DD}$ is the voltage applied to the RC combination circuit, $V_C$ is the voltage of the capacitor, and $R_{ref}$ is the resistance of the reference resistor.

Figure 26:
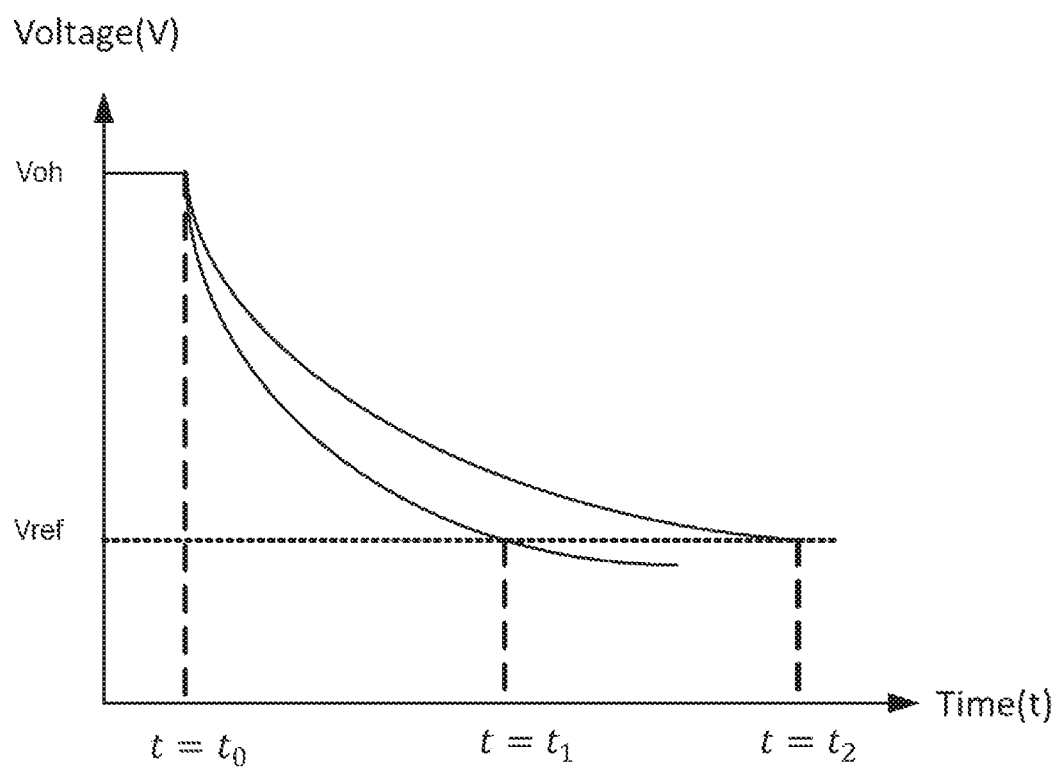
FIG. 26 shows the decrease of the voltage of a capacitor according to some embodiments of the present disclosure.

FIG. 26 shows the decrease of the voltage of capacitor according to the present disclosure. When the voltage of the capacitor 2404 is indicated as $V_{oh}$ and discharged, the calculation of the resistance $R_S$ may be calculated based on Equations 9, 10, and 11.

$$V_{ref} = V_{oh} * e^{\frac{-t}{RC}}, \qquad \text{Equation 9}$$

$$t = -RC * \ln\left(\frac{V_{ref}}{V_{oh}}\right), \text{ and} \qquad \text{Equation 10}$$

$$R_s = \left(\frac{t_2}{t_1}\right)R_{ref}, \qquad \text{Equation 11}$$

where $V_{ref}$ is the reference voltage applied to the comparator 2405, and $R_{ref}$ is the resistance of the reference resistor.

It should be noted that the description of the diagram is provided for illustration purposes. For persons having ordinary skills in the art, adjustments and modifications may be made without departing from the principle or spirit of the present disclosure. Therefore, it is given that the present disclosure should not be limited by the specific description herein. For example, the MCU 2401 may not include the comparator 2405 and an external comparator may be coupled to MCU for the measuring procedure cooperating with Input/Output interrupt or a timer. As another example, an additional Input/Output may be connected to the point A for charging the capacitor 2404 or a resistor in series for avoiding self-heat. Such alternatives, modifications, and variations will also be in the scope of this disclosure.

Having thus described the basic concepts, it may be rather apparent to those skilled in the art after reading this detailed disclosure that the foregoing detailed disclosure is intended to be presented by way of example only and is not limiting.

Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure. In addition, the term "logic" is representative of hardware, firmware, software (or any combination thereof) to perform one or more functions. For instance, examples of "hardware" include, but are not limited to, an integrated circuit, a finite state machine, or even combinatorial logic. The integrated circuit may take the form of a processor such as a microprocessor, an application specific integrated circuit, a digital signal processor, a micro-controller, or the like.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "circuit," "unit," "module," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device. In addition, the financial management system disclosed herein may be implemented as a firmware, firmware/software combination, firmware/hardware combination, or a hardware/firmware/software combination.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

What is claimed is:

1. An apparatus comprising:
   a storage device that stores a library of calibration formulas and calibration parameters associated with one or more of the calibration formulas, wherein
      the calibration parameter associated with a calibration formula is stored in a format having at least a first part and a second part, wherein
         the first part indicates a measurement range for the calibration formula, and
         the second part includes a plurality of segments, each of which corresponds to a segment of the measurement range and a value to be used in the associated calibration formula;
   a communication module that retrieves information from a sensor;
   an energy harvesting module configured to harvest various forms of energy from an ambient environment in coordination with the communication module; and
   a computing center that selects, based on the retrieved information, a calibration formula and an associated calibration parameter from the library, and calibrates the retrieved information according to the selected calibration formula and at least one segment of the associated calibration parameter.

2. The apparatus of claim 1, wherein the energy harvesting module is configured to convert the harvested energy to power.

3. The apparatus of claim 2, wherein the energy harvested is converted to a direct current (DC).

4. The apparatus of claim 2, wherein the apparatus is configured to operate using the power.

5. The apparatus of claim 1, the harvested energy comprising thermal energy, solar energy, vibration energy, FM energy, bioenergy, or electromagnetic energy.

6. The apparatus of claim 1, the communication module comprising a radio-frequency (RF) interface or a sensor interface.

7. The apparatus of claim 1, the communication module conducting a wireless communication according to a wireless communication protocol.

8. The apparatus of claim 7, the wireless communication protocol comprising a near field communication (NFC) protocol, or a radio-frequency identification (RFID) protocol.

9. The apparatus of claim 1, wherein the retrieving of the information is performed according to a wireless communication.

10. The apparatus of claim 1 further comprising a control unit configured to select, based on the retrieved information, the calibration formula from the library.

11. The apparatus of claim 10, the control unit further controlling access to storage device.

12. The apparatus of claim 10, the control unit further setting different permissions for different users.

13. The apparatus of claim 1, the library comprising a calibrating formula based on a Steinhart-Hart equation, a Chebyshev fitting equation, a LUT (Look-Up-Table), an exponential equation, a Fourier equation, a Gaussian equation, an interpolant equation, a power equation, a rational equation, a smoothing spline equation, a sum of sine equation, or a Weibul equation.

14. The apparatus of claim 1, the information relating to temperature or humidity.

15. The apparatus of claim 1, wherein the apparatus is coupled to a flexible antenna.

16. A patch comprising:
a first layer; and
a second layer comprising an apparatus of claim 1.

17. The patch of claim 16, the first layer comprising a waterproof film or an adhesive material.

18. The patch of the claim 16 further comprising a third layer, the third layer comprising an adhesive material.

19. The patch of claim 16 comprising a flexible antenna.

* * * * *